United States Patent
Tsuji et al.

(10) Patent No.: US 9,567,637 B2
(45) Date of Patent: Feb. 14, 2017

(54) ASSOCIATION OF HTRA1 MUTATIONS AND FAMILIAL ISCHEMIC CEREBRAL SMALL-VESSEL DISEASE

(75) Inventors: Shoji Tsuji, Tokyo (JP); Osamu Onodera, Niigata (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 226 days.

(21) Appl. No.: 13/265,074

(22) PCT Filed: Apr. 20, 2010

(86) PCT No.: PCT/JP2010/057323
§ 371 (c)(1),
(2), (4) Date: Jan. 3, 2012

(87) PCT Pub. No.: WO2010/123136
PCT Pub. Date: Oct. 28, 2010

(65) Prior Publication Data
US 2012/0100536 A1    Apr. 26, 2012

Related U.S. Application Data

(60) Provisional application No. 61/170,762, filed on Apr. 20, 2009.

(51) Int. Cl.
*C12Q 1/68* (2006.01)
*C12P 19/34* (2006.01)

(52) U.S. Cl.
CPC ....... *C12Q 1/6883* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2009/0186076 A1 | 7/2009 | Kataoka et al. |
| 2010/0034806 A1 | 2/2010 | Dietz et al. |
| 2011/0212075 A1* | 9/2011 | Ehrmann .............. C12Q 1/683 424/94.64 |

FOREIGN PATENT DOCUMENTS

WO    2007/088651 A1    8/2007

OTHER PUBLICATIONS

Lee et al. (Inv Opth. & Visual Science, Jun. 2008, vol. 49, pp. 2613-2619).*
Hara et al,. "Linkage Analysis of Recessive Leukoencephalopathy with Alopecia and Spondylosis Deformans (CARASIL)," Niigata Medical Journal (2005) vol. 119, No. 11, pp. 695, with English translation.
Hara et al., "Assocation of HTRA1 Mutations and Familial Ischemic Cerebral Small-Vessel Disease," New England Journal of Medicine (Apr. 23, 2009) vol. 360, No. 17, pp. 1729-1739.
Oka et al., "HtrA1 serine protease inhibits signaling mediated by Tgf-beta family proteins," Development (2004) vol. 131, No. 5, pp. 1041-1053.
Launay et al., "HtrA1-dependent proteolysis of TGF-β controls both neuronal maturation and developmental survival", Cell Death and Differentiation, vol. 15, (2008) pp. 1408-1416.
Canadian Office Action issued in Canadian Patent Application No. 2,759,457 on Feb. 16, 2016.
Dewan et al., "HTRA1 Promoter Polymorphism in Wet Age-Rlated Macular Degeneration," Science vol. 314, (2006) pp. 989-992.
Gibbs et al., "Further mapping of 10q26 supports strong association of HTRA1 polymorphisms with age-related macular degeneration", Vision Research, vol. 48, No. 5 (2008) pp. 685-689.
Varga et al., "ANTI-TGF-β Therapy in Fibrosis: Recent Progress and Implications for Systemic Scierosis", Current Opinion in Rheumatology, vol. 20, No. 6, (2008) pp. 720-728.

* cited by examiner

*Primary Examiner* — Sarae Bausch
(74) *Attorney, Agent, or Firm* — Birch, Stewart, Kolasch & Birch, LLP

(57) ABSTRACT

The present invention provides a method of diagnosing a cerebrovascular disease in a human comprising the steps of: (a) measuring a mutation of HTRA1 gene in a test sample from said human; and (b) determining if the mutation of HTRA1 gene in said test sample correlates with a cerebrovascular disease in said human.

4 Claims, 9 Drawing Sheets
(4 of 9 Drawing Sheet(s) Filed in Color)

SEQUENCE LISTING

```
<160> NUMBER OF SEQ ID NOS: 42

<210> SEQ ID NO 1
<211> LENGTH: 1443
<212> TYPE: DNA
<213> ORGANISM: Homo sapiens
<220> FEATURE:
<221> NAME/KEY: CDS
<222> LOCATION: (1)..(1443)

<400> SEQUENCE: 1 atg cag atc ccg cgc gcc gct ctt ctc ccg ctg ctg ctg ctg ctg      48
Met Gln Ile Pro Arg Ala Ala Leu Leu Pro Leu Leu Leu Leu Leu
1               5                   10                  15 gcg gcg ccc gcc tcg gcg cag ctg tcc cgg gcc ggc cgc tcg gcg cct   96
```

|  |  |  |  |  |  |  |  |  |  |  |  |
|---|---|---|---|---|---|---|---|---|---|---|---|
| Ala | Ala | Pro | Ala | Ser | Ala | Gln | Leu | Ser | Arg | Ala | Gly | Arg | Ser | Ala | Pro |
|  |  |  | 20 |  |  |  | 25 |  |  |  | 30 |

```
ttg gcc gcc ggg tgc cca gac cgc tgc gag ccg gcg cgc tgc ccg ccg        144
Leu Ala Ala Gly Cys Pro Asp Arg Cys Glu Pro Ala Arg Cys Pro Pro
             35                  40                  45 cag ccg gag cac tgc gag ggc ggc cgg gcc cgg gac gcg tgc ggc tgc        192
Gln Pro Glu His Cys Glu Gly Gly Arg Ala Arg Asp Ala Cys Gly Cys
             50                  55                  60 tgc gag gtg tgc ggc gcg ccc gag ggc gcg tgc ggc ctg cag gag            240
Cys Glu Val Cys Gly Ala Pro Glu Gly Ala Cys Gly Leu Gln Glu
65                  70                  75                  80 ggc ccg tgc ggc gag ggg ctg cag tgc gtg gtg ccc ttc ggg gtg cca        288
Gly Pro Cys Gly Glu Gly Leu Gln Cys Val Val Pro Phe Gly Val Pro
             85                  90                  95 gcc tcg gcc acg gtg cgg cgg cgc gcg cag gcc ggc ctc tgt gtg tgc        336
Ala Ser Ala Thr Val Arg Arg Arg Ala Gln Ala Gly Leu Cys Val Cys
             100                 105                 110 gcc agc agc gag ccg gtg tgc ggc agc gac gcc aac acc tac gcc aac        384
Ala Ser Ser Glu Pro Val Cys Gly Ser Asp Ala Asn Thr Tyr Ala Asn
             115                 120                 125 ctg tgc cag ctg cgc gcc gcc agc cgc cgc tcc gag agg ctg cac cgg        432
Leu Cys Gln Leu Arg Ala Ala Ser Arg Arg Ser Glu Arg Leu His Arg
             130                 135                 140 ccg ccg gtc atc gtc ctg cag cgc gga gcc tgc ggc caa ggg cag gaa        480
Pro Pro Val Ile Val Leu Gln Arg Gly Ala Cys Gly Gln Gly Gln Glu
145                 150                 155                 160 gat ccc aac agt ttg cgc cat aaa tat aac ttt atc gcg gac gtg gtg        528
Asp Pro Asn Ser Leu Arg His Lys Tyr Asn Phe Ile Ala Asp Val Val
             165                 170                 175 gag aag atc gcc cct gcc gtg gtt cat atc gaa ttg ttt cgc aag ctt        576
Glu Lys Ile Ala Pro Ala Val Val His Ile Glu Leu Phe Arg Lys Leu
             180                 185                 190 ccg ttt tct aaa cga gag gtg ccg gtg gct agt ggg tct ggg ttt att        624
Pro Phe Ser Lys Arg Glu Val Pro Val Ala Ser Gly Ser Gly Phe Ile
             195                 200                 205 gtg tcg gaa gat gga ctg atc gtg aca aat gcc cac gtg gtg acc aac        672
Val Ser Glu Asp Gly Leu Ile Val Thr Asn Ala His Val Val Thr Asn
             210                 215                 220 aag cac cgg gtc aaa gtt gag ctg aag aac ggt gca act tac gaa gcc        720
Lys His Arg Val Lys Val Glu Leu Lys Asn Gly Ala Thr Tyr Glu Ala
225                 230                 235                 240 aaa atc aag gat gtg gat gag aaa gca gac atc gca ctc atc aaa att        768
Lys Ile Lys Asp Val Asp Glu Lys Ala Asp Ile Ala Leu Ile Lys Ile
             245                 250                 255 gac cac cag ggc aag ctg cct gtc ctg ctg ctt ggc cgc tcc tca gag        816
Asp His Gln Gly Lys Leu Pro Val Leu Leu Leu Gly Arg Ser Ser Glu
             260                 265                 270 ctg cgg ccg gga gag ttc gtg gtc gcc atc gga agc ccg ttt tcc ctt        864
Leu Arg Pro Gly Glu Phe Val Val Ala Ile Gly Ser Pro Phe Ser Leu
             275                 280                 285 caa aac aca gtc acc acc ggg atc gtg agc acc acc cag cga ggc ggc        912
Gln Asn Thr Val Thr Thr Gly Ile Val Ser Thr Thr Gln Arg Gly Gly
             290                 295                 300 aaa gag ctg ggg ctc cgc aac tca gac atg gac tac atc cag acc gac        960
Lys Glu Leu Gly Leu Arg Asn Ser Asp Met Asp Tyr Ile Gln Thr Asp
305                 310                 315                 320 gcc atc atc aac tat gga aac tcg gga ggc ccg tta gta aac ctg gac       1008
Ala Ile Ile Asn Tyr Gly Asn Ser Gly Gly Pro Leu Val Asn Leu Asp
             325                 330                 335
```

```
ggt gaa gtg att gga att aac act ttg aaa gtg aca gct gga atc tcc    1056
Gly Glu Val Ile Gly Ile Asn Thr Leu Lys Val Thr Ala Gly Ile Ser
            340                 345                 350 ttt gca atc cca tct gat aag att aaa aag ttc ctc acg gag tcc cat    1104
Phe Ala Ile Pro Ser Asp Lys Ile Lys Lys Phe Leu Thr Glu Ser His
        355                 360                 365 gac cga cag gcc aaa gga aaa gcc atc acc aag aag aag tat att ggt    1152
Asp Arg Gln Ala Lys Gly Lys Ala Ile Thr Lys Lys Lys Tyr Ile Gly
    370                 375                 380 atc cga atg atg tca ctc acg tcc agc aaa gcc aaa gag ctg aag gac    1200
Ile Arg Met Met Ser Leu Thr Ser Ser Lys Ala Lys Glu Leu Lys Asp
385                 390                 395                 400 cgg cac cgg gac ttc cca gac gtg atc tca gga gcg tat ata att gaa    1248
Arg His Arg Asp Phe Pro Asp Val Ile Ser Gly Ala Tyr Ile Ile Glu
                405                 410                 415 gta att cct gat acc cca gca gaa gct ggt ggt ctc aag gaa aac gac    1296
Val Ile Pro Asp Thr Pro Ala Glu Ala Gly Gly Leu Lys Glu Asn Asp
            420                 425                 430 gtc ata atc agc atc aat gga cag tcc gtg gtc tcc gcc aat gat gtc    1344
Val Ile Ile Ser Ile Asn Gly Gln Ser Val Val Ser Ala Asn Asp Val
        435                 440                 445 agc gac gtc att aaa agg gaa agc acc ctg aac atg gtg gtc cgc agg    1392
Ser Asp Val Ile Lys Arg Glu Ser Thr Leu Asn Met Val Val Arg Arg
    450                 455                 460 ggt aat gaa gat atc atg atc aca gtg att ccc gaa gaa att gac cca    1440
Gly Asn Glu Asp Ile Met Ile Thr Val Ile Pro Glu Glu Ile Asp Pro
465                 470                 475                 480 tag                                                                1443

<210> SEQ ID NO 2
<211> LENGTH: 480
<212> TYPE: PRT
<213> ORGANISM: Homo sapiens

<400> SEQUENCE: 2

Met Gln Ile Pro Arg Ala Ala Leu Leu Pro Leu Leu Leu Leu Leu Leu
1               5                   10                  15

Ala Ala Pro Ala Ser Ala Gln Leu Ser Arg Ala Gly Arg Ser Ala Pro
            20                  25                  30

Leu Ala Ala Gly Cys Pro Asp Arg Cys Glu Pro Ala Arg Cys Pro Pro
        35                  40                  45

Gln Pro Glu His Cys Glu Gly Gly Arg Ala Arg Asp Ala Cys Gly Cys
    50                  55                  60

Cys Glu Val Cys Gly Ala Pro Glu Gly Ala Ala Cys Gly Leu Gln Glu
65                  70                  75                  80

Gly Pro Cys Gly Glu Gly Leu Gln Cys Val Val Pro Phe Gly Val Pro
                85                  90                  95

Ala Ser Ala Thr Val Arg Arg Arg Ala Gln Ala Gly Leu Cys Val Cys
            100                 105                 110

Ala Ser Ser Glu Pro Val Cys Gly Ser Asp Ala Asn Thr Tyr Ala Asn
        115                 120                 125

Leu Cys Gln Leu Arg Ala Ala Ser Arg Arg Ser Glu Arg Leu His Arg
    130                 135                 140

Pro Pro Val Ile Val Leu Gln Arg Gly Ala Cys Gly Gln Gly Gln Glu
145                 150                 155                 160

Asp Pro Asn Ser Leu Arg His Lys Tyr Asn Phe Ile Ala Asp Val Val
                165                 170                 175
```

```
Glu Lys Ile Ala Pro Ala Val Val His Ile Glu Leu Phe Arg Lys Leu
            180                 185                 190

Pro Phe Ser Lys Arg Glu Val Pro Val Ala Ser Gly Ser Gly Phe Ile
        195                 200                 205

Val Ser Glu Asp Gly Leu Ile Val Thr Asn Ala His Val Val Thr Asn
    210                 215                 220

Lys His Arg Val Lys Val Glu Leu Lys Asn Gly Ala Thr Tyr Glu Ala
225                 230                 235                 240

Lys Ile Lys Asp Val Asp Glu Lys Ala Asp Ile Ala Leu Ile Lys Ile
                245                 250                 255

Asp His Gln Gly Lys Leu Pro Val Leu Leu Leu Gly Arg Ser Ser Glu
            260                 265                 270

Leu Arg Pro Gly Glu Phe Val Val Ala Ile Gly Ser Pro Phe Ser Leu
        275                 280                 285

Gln Asn Thr Val Thr Thr Gly Ile Val Ser Thr Thr Gln Arg Gly Gly
    290                 295                 300

Lys Glu Leu Gly Leu Arg Asn Ser Asp Met Asp Tyr Ile Gln Thr Asp
305                 310                 315                 320

Ala Ile Ile Asn Tyr Gly Asn Ser Gly Gly Pro Leu Val Asn Leu Asp
                325                 330                 335

Gly Glu Val Ile Gly Ile Asn Thr Leu Lys Val Thr Ala Gly Ile Ser
            340                 345                 350

Phe Ala Ile Pro Ser Asp Lys Ile Lys Lys Phe Leu Thr Glu Ser His
        355                 360                 365

Asp Arg Gln Ala Lys Gly Lys Ala Ile Thr Lys Lys Lys Tyr Ile Gly
    370                 375                 380

Ile Arg Met Met Ser Leu Thr Ser Ser Lys Ala Lys Glu Leu Lys Asp
385                 390                 395                 400

Arg His Arg Asp Phe Pro Asp Val Ile Ser Gly Ala Tyr Ile Ile Glu
                405                 410                 415

Val Ile Pro Asp Thr Pro Ala Glu Ala Gly Gly Leu Lys Glu Asn Asp
            420                 425                 430

Val Ile Ile Ser Ile Asn Gly Gln Ser Val Val Ser Ala Asn Asp Val
        435                 440                 445

Ser Asp Val Ile Lys Arg Glu Ser Thr Leu Asn Met Val Val Arg Arg
    450                 455                 460

Gly Asn Glu Asp Ile Met Ile Thr Val Ile Pro Glu Glu Ile Asp Pro
465                 470                 475                 480

<210> SEQ ID NO 3
<211> LENGTH: 2217
<212> TYPE: DNA
<213> ORGANISM: Homo sapiens
<220> FEATURE:
<221> NAME/KEY: CDS
<222> LOCATION: (883)..(2055)

<400> SEQUENCE: 3
ccccgccgcc gccgcccttc gcgccctggg ccatctccct cccacctccc tccgcggagc      60
agccagacag cgagggcccc ggccgggggc agggggacg ccccgtccgg ggcaccccc      120 cggctctgag ccgcccgcgg ggccggcctc ggcccggagc ggaggaagga gtcgccgagg    180
agcagcctga ggccccagag tctgagacga gccgccgccg ccccgccac tgcggggagg    240 agggggagga ggagcgggag gagggacgag ctggtcggga gaagaggaaa aaaactttg    300 agacttttcc gttgccgctg ggagccggag gcgcggggac ctcttggcgc gacgctgccc    360
```

-continued

```
cgcgaggagg caggacttgg ggaccccaga ccgcctccct tgccgccgg ggacgcttgc      420 tccctccctg ccccctacac ggcgtccctc aggcgcccc attccggacc agccctcggg       480
agtcgccgac ccggcctccc gcaaagactt ttccccagac ctcgggcgca ccccctgcac     540
gccgccttca tccccggcct gtctcctgag ccccgcgca tcctagaccc tttctcctcc      600
aggagacgga tctctctccg acctgccaca gatcccctat tcaagaccac ccaccttctg    660
gtaccagatc gcgcccatct aggttatttc cgtgggatac tgagacaccc ccggtccaag    720
cctcccctcc accactgcgc ccttctccct gaggacctca gctttccctc gaggccctcc   780
taccttttgc cggagacccc cagcccctg caggggcggg gcctcccac cacaccagcc      840 ctgttcgcgc tctcggcagt gccgggggc gccgcctccc cc atg ccg ccc tcc       894
                                              Met Pro Pro Ser
                                              1 ggg ctg cgg ctg ctg ccg ctg ctg cta ccg ctg ctg tgg cta ctg gtg     942
Gly Leu Arg Leu Leu Pro Leu Leu Leu Pro Leu Leu Trp Leu Leu Val
5                  10                 15                 20 ctg acg cct ggc cgg ccg gcc gcg gga cta tcc acc tgc aag act atc    990
Leu Thr Pro Gly Arg Pro Ala Ala Gly Leu Ser Thr Cys Lys Thr Ile
            25                 30                 35 gac atg gag ctg gtg aag cgg aag cgc atc gag gcc atc cgc ggc cag   1038
Asp Met Glu Leu Val Lys Arg Lys Arg Ile Glu Ala Ile Arg Gly Gln
                40                 45                 50 atc ctg tcc aag ctg cgg ctc gcc agc ccc ccg agc cag ggg gag gtg   1086
Ile Leu Ser Lys Leu Arg Leu Ala Ser Pro Pro Ser Gln Gly Glu Val
            55                 60                 65 ccg ccc ggc ccg ctg ccc gag gcc gtg ctc gcc ctg tac aac agc acc   1134
Pro Pro Gly Pro Leu Pro Glu Ala Val Leu Ala Leu Tyr Asn Ser Thr
        70                 75                 80 cgc gac cgg gtg gcc ggg gag agt gca gaa ccg gag ccc gag cct gag   1182
Arg Asp Arg Val Ala Gly Glu Ser Ala Glu Pro Glu Pro Glu Pro Glu
85                 90                 95                 100 gcc gac tac tac gcc aag gag gtc acc cgc gtg cta atg gtg gaa acc   1230
Ala Asp Tyr Tyr Ala Lys Glu Val Thr Arg Val Leu Met Val Glu Thr
                105                110                115 cac aac gaa atc tat gac aag ttc aag cag agt aca cac agc ata tat   1278
His Asn Glu Ile Tyr Asp Lys Phe Lys Gln Ser Thr His Ser Ile Tyr
            120                125                130 atg ttc ttc aac aca tca gag ctc cga gaa gcg gta cct gaa ccc gtg   1326
Met Phe Phe Asn Thr Ser Glu Leu Arg Glu Ala Val Pro Glu Pro Val
        135                140                145 ttg ctc tcc cgg gca gag ctg cgt ctg ctg agg ctc aag tta aaa gtg   1374
Leu Leu Ser Arg Ala Glu Leu Arg Leu Leu Arg Leu Lys Leu Lys Val
    150                155                160 gag cag cac gtg gag ctg tac cag aaa tac agc aac aat tcc tgg cga   1422
Glu Gln His Val Glu Leu Tyr Gln Lys Tyr Ser Asn Asn Ser Trp Arg
165                170                175                180 tac ctc agc aac cgg ctg ctg gca ccc agc gac tcg cca gag tgg tta   1470
Tyr Leu Ser Asn Arg Leu Leu Ala Pro Ser Asp Ser Pro Glu Trp Leu
                185                190                195 tct ttt gat gtc acc gga gtt gtg cgg cag tgg ttg agc cgt gga ggg   1518
Ser Phe Asp Val Thr Gly Val Val Arg Gln Trp Leu Ser Arg Gly Gly
            200                205                210 gaa att gag ggc ttt cgc ctt agc gcc cac tgc tcc tgt gac agc agg   1566
Glu Ile Glu Gly Phe Arg Leu Ser Ala His Cys Ser Cys Asp Ser Arg
        215                220                225 gat aac aca ctg caa gtg gac atc aac ggg ttc act acc ggc cgc cga   1614
Asp Asn Thr Leu Gln Val Asp Ile Asn Gly Phe Thr Thr Gly Arg Arg
```

```
                    230                 235                 240
ggt gac ctg gcc acc att cat ggc atg aac cgg cct ttc ctg ctt ctc    1662
Gly Asp Leu Ala Thr Ile His Gly Met Asn Arg Pro Phe Leu Leu Leu
245                 250                 255                 260 atg gcc acc ccg ctg gag agg gcc cag cat ctg caa agc tcc cgg cac    1710
Met Ala Thr Pro Leu Glu Arg Ala Gln His Leu Gln Ser Ser Arg His
                265                 270                 275 cgc cga gcc ctg gac acc aac tat tgc ttc agc tcc acg gag aag aac    1758
Arg Arg Ala Leu Asp Thr Asn Tyr Cys Phe Ser Ser Thr Glu Lys Asn
            280                 285                 290 tgc tgc gtg cgg cag ctg tac att gac ttc cgc aag gac ctc ggc tgg    1806
Cys Cys Val Arg Gln Leu Tyr Ile Asp Phe Arg Lys Asp Leu Gly Trp
        295                 300                 305 aag tgg atc cac gag ccc aag ggc tac cat gcc aac ttc tgc ctc ggg    1854
Lys Trp Ile His Glu Pro Lys Gly Tyr His Ala Asn Phe Cys Leu Gly
    310                 315                 320 ccc tgc ccc tac att tgg agc ctg gac acg cag tac agc aag gtc ctg    1902
Pro Cys Pro Tyr Ile Trp Ser Leu Asp Thr Gln Tyr Ser Lys Val Leu
325                 330                 335                 340 gcc ctg tac aac cag cat aac ccg ggc gcc tcg gcg gcg ccg tgc tgc    1950
Ala Leu Tyr Asn Gln His Asn Pro Gly Ala Ser Ala Ala Pro Cys Cys
                345                 350                 355 gtg ccg cag gcg ctg gag ccg ctg ccc atc gtg tac tac gtg ggc cgc    1998
Val Pro Gln Ala Leu Glu Pro Leu Pro Ile Val Tyr Tyr Val Gly Arg
            360                 365                 370 aag ccc aag gtg gag cag ctg tcc aac atg atc gtg cgc tcc tgc aag    2046
Lys Pro Lys Val Glu Gln Leu Ser Asn Met Ile Val Arg Ser Cys Lys
        375                 380                 385 tgc agc tga ggtcccgccc cgccccgccc cgcccggca ggcccggccc             2095
Cys Ser
    390 caccccgccc cgccccgct gccttgccca tgggggctgt atttaaggac accgtgccc    2155 caagcccacc tggggcccca ttaaagatgg agagaggact gcggaaaaaa aaaaaaaaa   2215 aa                                                                 2217

<210> SEQ ID NO 4
<211> LENGTH: 390
<212> TYPE: PRT
<213> ORGANISM: Homo sapiens

<400> SEQUENCE: 4

Met Pro Pro Ser Gly Leu Arg Leu Leu Pro Leu Leu Pro Leu Leu
1               5                   10                  15

Trp Leu Leu Val Leu Thr Pro Gly Arg Pro Ala Ala Gly Leu Ser Thr
                20                  25                  30

Cys Lys Thr Ile Asp Met Glu Leu Val Lys Arg Lys Arg Ile Glu Ala
            35                  40                  45

Ile Arg Gly Gln Ile Leu Ser Lys Leu Arg Leu Ala Ser Pro Pro Ser
        50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125
```

```
His Ser Ile Tyr Met Phe Phe Asn Thr Ser Glu Leu Arg Glu Ala Val
        130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
    370                 375                 380

Arg Ser Cys Lys Cys Ser
385                 390

<210> SEQ ID NO 5
<211> LENGTH: 20
<212> TYPE: DNA
<213> ORGANISM: Artificial Sequence
<220> FEATURE:
<223> OTHER INFORMATION: Synthetic DNA

<400> SEQUENCE: 5
attacaggca tgagccactg                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic DNA

<400> SEQUENCE: 6
ttgtctgcca tacatgctgc                                               20

<210> SEQ ID NO 7
<211> LENGTH: 20
```

<212> TYPE: DNA
<213> ORGANISM: Artificial Sequence
<220> FEATURE:
<223> OTHER INFORMATION: Synthetic DNA

<400> SEQUENCE: 7
gggaactaag agatgctgag                                           20

<210> SEQ ID NO 8
<211> LENGTH: 21
<212> TYPE: DNA
<213> ORGANISM: Artificial Sequence
<220> FEATURE:
<223> OTHER INFORMATION: Synthetic DNA

<400> SEQUENCE: 8
tgttgctacc ttttgcatct c                                         21

<210> SEQ ID NO 9
<211> LENGTH: 21
<212> TYPE: DNA
<213> ORGANISM: Artificial Sequence
<220> FEATURE:
<223> OTHER INFORMATION: Synthetic DNA

<400> SEQUENCE: 9
aaaactaggc ttgcccacaa g                                         21

<210> SEQ ID NO 10
<211> LENGTH: 20
<212> TYPE: DNA
<213> ORGANISM: Artificial Sequence
<220> FEATURE:
<223> OTHER INFORMATION: Synthetic DNA

<400> SEQUENCE: 10
agggtgccac ttgctatttg                                           20

<210> SEQ ID NO 11
<211> LENGTH: 21
<212> TYPE: DNA
<213> ORGANISM: Artificial Sequence
<220> FEATURE:
<223> OTHER INFORMATION: Synthetic DNA

<400> SEQUENCE: 11
acgagacaag acttctttca g                                         21

<210> SEQ ID NO 12
<211> LENGTH: 21
<212> TYPE: DNA
<213> ORGANISM: Artificial Sequence
<220> FEATURE:
<223> OTHER INFORMATION: Synthetic DNA

<400> SEQUENCE: 12
ccacagtagt aacctcttta g                                         21

<210> SEQ ID NO 13
<211> LENGTH: 21
<212> TYPE: DNA
<213> ORGANISM: Artificial Sequence
<220> FEATURE:
<223> OTHER INFORMATION: Synthetic DNA

<400> SEQUENCE: 13
aaaattaccg ggcacattca c                                             21

<210> SEQ ID NO 14
<211> LENGTH: 21
<212> TYPE: DNA
<213> ORGANISM: Artificial Sequence
<220> FEATURE:
<223> OTHER INFORMATION: Synthetic DNA

<400> SEQUENCE: 14
ctcatgatac gttaagggaa g                                             21

<210> SEQ ID NO 15
<211> LENGTH: 18
<212> TYPE: DNA
<213> ORGANISM: Artificial Sequence
<220> FEATURE:
<223> OTHER INFORMATION: Synthetic DNA

<400> SEQUENCE: 15
cgccatcatc aactatcg                                                 18

<210> SEQ ID NO 16
<211> LENGTH: 20
<212> TYPE: DNA
<213> ORGANISM: Artificial Sequence
<220> FEATURE:
<223> OTHER INFORMATION: Synthetic DNA

<400> SEQUENCE: 16
gtcaaaagtc ttgagtgtcc                                               20

<210> SEQ ID NO 17
<211> LENGTH: 19
<212> TYPE: DNA
<213> ORGANISM: Artificial Sequence
<220> FEATURE:
<223> OTHER INFORMATION: Synthetic DNA

<400> SEQUENCE: 17
ccagcactat ctccacatc                                                19

<210> SEQ ID NO 18
<211> LENGTH: 19
<212> TYPE: DNA
<213> ORGANISM: Artificial Sequence
<220> FEATURE:
<223> OTHER INFORMATION: Synthetic DNA

<400> SEQUENCE: 18
gcagcgtctc gttcagatc                                                19

<210> SEQ ID NO 19
<211> LENGTH: 20
<212> TYPE: DNA
<213> ORGANISM: Artificial Sequence
<220> FEATURE:
<223> OTHER INFORMATION: Synthetic DNA

<400> SEQUENCE: 19
cttctacaat gagctgcgtg                                               20

<210> SEQ ID NO 20
<211> LENGTH: 21
<212> TYPE: DNA
<213> ORGANISM: Artificial Sequence

```
<220> FEATURE:
<223> OTHER INFORMATION: Synthetic DNA

<400> SEQUENCE: 20
gtctcaaaca tgatctgggt c                                              21

<210> SEQ ID NO 21
<211> LENGTH: 5
<212> TYPE: PRT
<213> ORGANISM: Homo sapiens
<220> FEATURE:
<221> NAME/KEY: misc_feature
<222> LOCATION: (1)..(5)
<223> OTHER INFORMATION: HTRA1

<400> SEQUENCE: 21

Asp Ile Ala Leu Ile
1               5

<210> SEQ ID NO 22
<211> LENGTH: 5
<212> TYPE: PRT
<213> ORGANISM: Homo sapiens
<220> FEATURE:
<221> NAME/KEY: misc_feature
<222> LOCATION: (1)..(5)
<223> OTHER INFORMATION: HTRA1

<400> SEQUENCE: 22

Gly Ile Val Ser Thr
1               5

<210> SEQ ID NO 23
<211> LENGTH: 5
<212> TYPE: PRT
<213> ORGANISM: Homo sapiens
<220> FEATURE:
<221> NAME/KEY: misc_feature
<222> LOCATION: (1)..(5)
<223> OTHER INFORMATION: HTRA2

<400> SEQUENCE: 23

Asp Ile Ala Thr Leu
1               5

<210> SEQ ID NO 24
<211> LENGTH: 5
<212> TYPE: PRT
<213> ORGANISM: Homo sapiens
<220> FEATURE:
<221> NAME/KEY: misc_feature
<222> LOCATION: (1)..(5)
<223> OTHER INFORMATION: HTRA2

<400> SEQUENCE: 24

Gly Ile Val Ser Ser
1               5

<210> SEQ ID NO 25
<211> LENGTH: 5
<212> TYPE: PRT
<213> ORGANISM: Homo sapiens
<220> FEATURE:
<221> NAME/KEY: misc_feature
<222> LOCATION: (1)..(5)
<223> OTHER INFORMATION: HTRA3

<400> SEQUENCE: 25
```

Asp Ile Ala Thr Ile
1               5

<210> SEQ ID NO 26
<211> LENGTH: 5
<212> TYPE: PRT
<213> ORGANISM: Homo sapiens
<220> FEATURE:
<221> NAME/KEY: misc_feature
<222> LOCATION: (1)..(5)
<223> OTHER INFORMATION: HTRA3

<400> SEQUENCE: 26

Gly Ile Val Ser Thr
1               5

<210> SEQ ID NO 27
<211> LENGTH: 5
<212> TYPE: PRT
<213> ORGANISM: Homo sapiens
<220> FEATURE:
<221> NAME/KEY: misc_feature
<222> LOCATION: (1)..(5)
<223> OTHER INFORMATION: HTRA4

<400> SEQUENCE: 27

Asp Leu Ala Val Ile
1               5

<210> SEQ ID NO 28
<211> LENGTH: 5
<212> TYPE: PRT
<213> ORGANISM: Homo sapiens
<220> FEATURE:
<221> NAME/KEY: misc_feature
<222> LOCATION: (1)..(5)
<223> OTHER INFORMATION: HTRA4

<400> SEQUENCE: 28

Gly Ile Val Ser Thr
1               5

<210> SEQ ID NO 29
<211> LENGTH: 5
<212> TYPE: PRT
<213> ORGANISM: Mus musculus
<220> FEATURE:
<221> NAME/KEY: misc_feature
<222> LOCATION: (1)..(5)
<223> OTHER INFORMATION: HTRA1

<400> SEQUENCE: 29

Asp Ile Ala Leu Ile
1               5

<210> SEQ ID NO 30
<211> LENGTH: 5
<212> TYPE: PRT
<213> ORGANISM: Mus musculus
<220> FEATURE:
<221> NAME/KEY: misc_feature
<222> LOCATION: (1)..(5)
<223> OTHER INFORMATION: HTRA1

<400> SEQUENCE: 30

Gly Ile Val Ser Thr
1               5

-continued

```
<210> SEQ ID NO 31
<211> LENGTH: 5
<212> TYPE: PRT
<213> ORGANISM: Drosophila melanogaster
<220> FEATURE:
<221> NAME/KEY: misc_feature
<222> LOCATION: (1)..(5)
<223> OTHER INFORMATION: HTRA1

<400> SEQUENCE: 31

Asp Ile Ala Leu Ile
1               5

<210> SEQ ID NO 32
<211> LENGTH: 5
<212> TYPE: PRT
<213> ORGANISM: Drosophila melanogaster
<220> FEATURE:
<221> NAME/KEY: misc_feature
<222> LOCATION: (1)..(5)
<223> OTHER INFORMATION: HTRA1

<400> SEQUENCE: 32

Gly Ile Val Ser Thr
1               5

<210> SEQ ID NO 33
<211> LENGTH: 5
<212> TYPE: PRT
<213> ORGANISM: Rattus novegicus
<220> FEATURE:
<221> NAME/KEY: misc_feature
<222> LOCATION: (1)..(5)
<223> OTHER INFORMATION: HTRA1

<400> SEQUENCE: 33

Asp Leu Ala Thr Leu
1               5

<210> SEQ ID NO 34
<211> LENGTH: 5
<212> TYPE: PRT
<213> ORGANISM: Rattus novegicus
<220> FEATURE:
<221> NAME/KEY: misc_feature
<222> LOCATION: (1)..(5)
<223> OTHER INFORMATION: HTRA1

<400> SEQUENCE: 34

Gly Val Ile Ser Ser
1               5

<210> SEQ ID NO 35
<211> LENGTH: 5
<212> TYPE: PRT
<213> ORGANISM: Arabidopsis thaliana
<220> FEATURE:
<221> NAME/KEY: misc_feature
<222> LOCATION: (1)..(5)
<223> OTHER INFORMATION: HTRA1

<400> SEQUENCE: 35

Asp Ile Ala Leu Val
1               5

<210> SEQ ID NO 36
<211> LENGTH: 5
<212> TYPE: PRT
<213> ORGANISM: Arabidopsis thaliana
```

```
<220> FEATURE:
<221> NAME/KEY: misc_feature
<222> LOCATION: (1)..(5)
<223> OTHER INFORMATION: HTRA1

<400> SEQUENCE: 36

Gly Ile Val Ser Cys
1               5

<210> SEQ ID NO 37
<211> LENGTH: 5
<212> TYPE: PRT
<213> ORGANISM: Saccharomyces cerevisiae
<220> FEATURE:
<221> NAME/KEY: misc_feature
<222> LOCATION: (1)..(5)
<223> OTHER INFORMATION: HTRA1

<400> SEQUENCE: 37

Asn Phe Ala Ile Val
1               5

<210> SEQ ID NO 38
<211> LENGTH: 5
<212> TYPE: PRT
<213> ORGANISM: Saccharomyces cerevisiae
<220> FEATURE:
<221> NAME/KEY: misc_feature
<222> LOCATION: (1)..(5)
<223> OTHER INFORMATION: HTRA1

<400> SEQUENCE: 38

Asp Ile Ser Ser Val
1               5

<210> SEQ ID NO 39
<211> LENGTH: 5
<212> TYPE: PRT
<213> ORGANISM: Escherichia coli
<220> FEATURE:
<221> NAME/KEY: misc_feature
<222> LOCATION: (1)..(5)
<223> OTHER INFORMATION: HTRA1

<400> SEQUENCE: 39

Asp Ile Ala Leu Ile
1               5

<210> SEQ ID NO 40
<211> LENGTH: 5
<212> TYPE: PRT
<213> ORGANISM: Escherichia coli
<220> FEATURE:
<221> NAME/KEY: misc_feature
<222> LOCATION: (1)..(5)
<223> OTHER INFORMATION: HTRA1

<400> SEQUENCE: 40

Gly Ile Val Ser Ala
1               5

<210> SEQ ID NO 41
<211> LENGTH: 15
<212> TYPE: DNA
<213> ORGANISM: Homo sapiens

<400> SEQUENCE: 41
catgacygac aggcc                                                      15
```

```
<210> SEQ ID NO 42
<211> LENGTH: 15
<212> TYPE: DNA
<213> ORGANISM: Homo sapiens

<400> SEQUENCE: 42
catgaccgac aggcc                                                      15
```

ASSOCIATION OF HTRA1 MUTATIONS AND FAMILIAL ISCHEMIC CEREBRAL SMALL-VESSEL DISEASE

CROSS REFERENCE TO RELATED APPLICATIONS

This application is the National Phase of PCT/JP2010/057323 filed on Apr. 20, 2010. which claims priority under 35 U.S.C. 119(e) to U.S. Provisional Application No. 61/170,762 filed on Apr. 20, 2009, all of which are hereby expressly incorporated by reference into the present application.

TECHNICAL FIELD

The present invention relates to a method of diagnosing cerebral autosomal recessive arteriopathy with subcortical infarcts and leukoencephalopathy (CARASIL).

BACKGROUND ART

Hypertension is a well-known risk factor for nonhereditary cerebral small-vessel disease.[1] Genetic causes have been identified for hereditary cerebral small-vessel diseases: cerebral autosomal dominant arteriopathy with subcortical infarcts and leukoencephalopathy;[2] autosomal dominant retinal vasculopathy with cerebral leukodystrophy;[3] brain small-vessel disease with hemorrhage;[4] and familial cerebral amyloid angiopathies.[5] Although arteriopathy in these cerebral small-vessel diseases is well documented, little is known about its genetic basis.

A cerebral autosomal recessive arteriopathy with subcortical infarcts and leukoencephalopathy (CARASIL) is characterized by nonhypertensive cerebral small-vessel arteriopathy with subcortical infarcts, alopecia, and spondylosis, with onset in early adulthood.[6-8] On neuropathological examination, arteriosclerosis associated with intimal thickening and dense collagen fibers, loss of vascular smooth muscle cells, and hyaline degeneration of the media was observed in cerebral small arteries.[7-9] These pathological findings resemble those observed in patients with nonhereditary ischemic cerebral small-vessel disease.[7-11]

DISCLOSURE OF INVENTION

Summary of Invention

In the present invention, the present inventors show that mutations in HTRA1, a gene encoding HtrA serine peptidase 1, cause CARASIL.

The genetic cause of cerebral autosomal recessive arteriopathy with subcortical infarcts and leukoencephalopathy (CARASIL), which is ischemic, nonhypertensive cerebral small-vessel disease with alopecia and spondylosis, has not been reported.

We carried out a genomewide linkage analysis and fine mapped the implicated region of five families with CARASIL, followed by sequence analysis of a candidate gene. We carried out functional analysis of wildtype and mutant gene products, and assayed transforming growth factor β (TGF-β) family signaling, and gene and protein expression in the small arteries in the cerebrum of two patients with CARASIL.

We observed linkage of the disease to the 2.4-Mb region on chromosome 10q, which contains the HTRA1 gene. HTRA1 is a serine protease that represses signaling by TGF-β family members. Sequence analysis revealed two nonsense mutations and two missense mutations in HTRA1. The missense mutations and one of the nonsense mutations resulted in protein products that had comparatively low levels of protease activity and did not repress TGF-β family signaling. The other nonsense mutation resulted in the loss of HTRA1 protein by nonsense-mediated mRNA decay. Immunohistochemistry of the cerebral small arteries in affected persons showed increased expression of ED-A fibronectin and versican in the thickened intima, and of TGF-β in the media.

CARASIL is caused by mutations in the HTRA1 gene. Our findings indicate a link between repressed inhibition of TGF-β family signaling and ischemic cerebral small-vessel disease, alopecia, and spondylosis.

The present invention describes the use in the diagnosis and detecting of cerebrovascular disease in a human. A mutation of HTRA1 gene is indicative of some type of cerebrovascular disease.

In one embodiment, the present invention is drawn to a method of diagnosing a cerebrovascular disease in a human comprising the steps of: (a) measuring a mutation of HTRA1 gene in a test sample from said human; and (b) determining if the mutation of HTRA1 gene in said test sample correlates with a cerebrovascular disease in said human.

In one embodiment, the present invention is drawn to a method of detecting a cerebrovascular disease in a human comprising the steps of: (a) measuring a mutation of HTRA1 gene in a test sample from said human; and (b) correlating the mutation of HTRA1 gene in said test sample with a cerebrovascular disease in said human.

The test sample may be selected from the group including but not limited to blood, serum, plasma, saliva, cerebral spinal fluid, oral mucosa and nail. In a preferred embodiment, the test sample is blood.

In a preferred embodiment, the cerebrovascular disease is selected from the group including but not limited to cerebral autosomal recessive arteriopathy with subcortical infarcts and leukoencephalopathy (CARASIL), acute cerebrovascular disease, ischemic cerebrovascular disease, Binswanger disease, leukoaraiosis, cerebral small vessel disease, and leukoencephalopatky.

In one embodiment, the present invention is drawn to a kit for diagnosing or detecting a cerebrovascular disease in a human, comprising a primer set for amplifying a mutant HTRA1 gene and a wild type HTRA1 gene.

In some embodiments, the determination or correlation step is a comparison between nucleotide sequence of test sample and a wild type nucleotide sequence of HTRA1 gene.

In one embodiment, the present invention is drawn to a pharmaceutical composition comprising a substance that inhibits signaling by TGF-β family proteins. In a preferred embodiment, the substance that inhibits signaling by TGF-β family proteins is siRNA, shRNA or decoy nucleic acid that targets a gene coding for TGF-β.

BRIEF DESCRIPTION OF DRAWINGS

The patent or application file contains at least one color drawing. Copies of this patent or patent application publication with color drawing will be provided by the USPTO upon request and payment of the necessary fee.

FIG. 1A: Families of Asian (Japanese) ancestral origin and some of their family members used in linkage analysis FIG. 1B: Gene map of location of HTRA1.

FIG. 1C: Diagram of homozygous nonsense and missense mutations.

FIG. 1D: Conservation of mutations. Left column sequences from top to bottom: SEQ ID NOs: 21, 23, 25, 27, 29, 31, 33, 35, 37, and 39. Right column sequences from top to bottom: SEQ ID NOs: 22, 24, 26, 28, 30, 32, 34, 36, 38, and 40.

FIGS. 1E, 1F, 1G, 1H and 1I: Evidence of diffuse white matter lesions on magnetic resonance imaging, autosomal recessive inheritance, onset of symptoms between their second and fifth decade, and spondylosis or alopecia (respectively).

FIG. 2A: Protease activity of N-Terminal deleted HtrA1s expressed in E. coli

FIG. 2B: Protease activity of full-length HtrA1s expressed in HEK293

FIG. 2C: Gel of Comlex of α1-antitrypsin and HtrA1 monomers

FIG. 3A: HTRA1 mRNA levels in control and R370X mutants.

FIG. 3B: Protein levels for wild-type HTRA1 and R370X HTRA1 mutant.

FIG. 3C: Analysis of HTRA1 of leukocytes from a heterozygous carrier of this R370X mutation. R370X Hetero genomic DNA (Family 2284 II-1) (SEQ ID NO: 41). R370X Hetero cDNA (Family 2285 II-1) (SEQ ID NO: 42).

FIG. 4A: Evidence of inability to repress signaling by the TGF-β family members TGF-β, BMP-4 and BMP-2 (FIG. 4A). As expected, none of the missense-mutated HTRA1 proteins repressed signaling by these molecules.

FIG. 4B: Evidence that none of the mutant HTRA1 proteins repressed the subsequent phosphorylation of Smad proteins (FIG. 4B).

FIG. 4C: Evidence of TGF-β signaling in fibroblasts from the subject with CARASIL with the R370X mutation.

FIG. 4D: Elevation of NOG mRNA in the probands.

FIGS. 4E-P: CARASIL patients carrying the R302X or A252T mutation showed increased expression of ED-A fibronectin (FIG. 4E, 4F, 4G, 4H) and versican (FIG. 4K) when compared with those of control subjects (FIGS. 4M, 4N and 4O). The result was confirmed by an in situ hybridization assay that used a probe for ED-A fibronectin (FIG. 4I, 4J). Moreover, the media of CARASIL patients exhibited elevated expression of TGF-β1 (FIG. 4L, 4P).

BEST MODE FOR CARRYING OUT THE INVENTION

Figure 1:
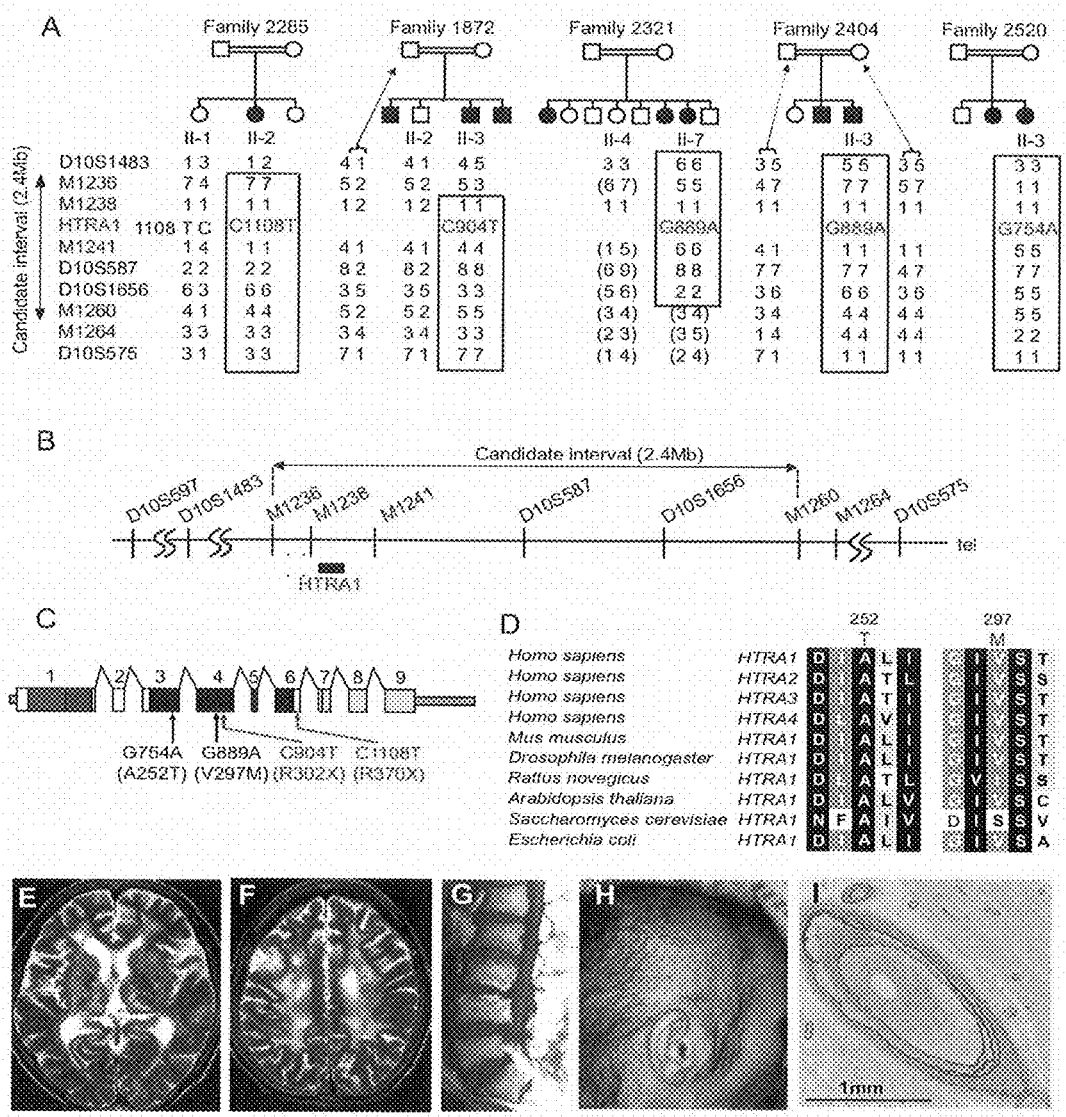
FIG. 1. Pedigrees and HTRA1 Mutations of Families with CARASIL.

1. Detection and Diagnosis of Genetic Mutation of HTRA1 Gene (1) Genetic Mutations of HTRA1 Gene Information on genetic mutations may be obtained by conventional methods for detecting genetic mutations. For example, the sequencing method, the PCR method, hybridization methods using a sequence-specific oligonucleotide as a template (e.g. TaqMan PCR method), and the like may be employed. The PCR method and the direct sequencing method may be used for detecting any type of genetic mutation.

In the present invention, preferred mutations for detecting or diagnosing cerebrovascular disease include but not limited to nonsense mutations and missense mutations of HTRA1 gene (Accession number: NM 002775 (SEQ ID NO:1)).

In the present invention, "mutant" or "mutation" means a protein or DNA resulting from a modification such as deletion, addition or substitution of one or more (for example one to ten, preferably, one to five) amino acids or nucleotides and includes substances which undergo disinhibition of TGF-β family signaling. For example, analysis of CARASIL has lead to the discovery of HTRA1 mutations such as, but not limited to A252T, V297M, R302X and R370X. A252T is a mutant resulting from substitution of the $252^{nd}$ alanine (Ala) by threonine (Thr) in the amino acid sequence of HTRA1 (SEQ ID NO:2). V297M is a mutant resulting from substitution of the $297^{th}$ valine (Val) by methionine (Met) in the amino acid sequence of HTRA1. R302X is a mutant resulting from substitution of the $302^{nd}$ arginine (Arg) by stop codone in the amino acid sequence of HTRA1. R370X is a mutant resulting from substitution of the $370^{nd}$ arginine (Arg) by stop codone in the amino acid sequence of HTRA1.

In the DNA sequence of HTRA1 gene, the nucleotide at position 1108 was changed from C to T, compared with wild type HTRA1 gene (SEQ ID NO:1). (Hereinafter, this mutation is expressed as "C1108→T". Other mutations will also be expressed in the same manner.) Besides, when compared with wild type HTRA1 gene (SEQ ID NO:1), the DNA sequence has mutations of G754→A, G889→A, C904→T or C1108→T In the present invention, a detection or diagnosis is performed based on, for example, the above-mentioned mutations.

(2) Direct Sequencing Assay

Mutations of HTRA1 gene can be detected by use of a direct sequencing method. In this assay, a DNA sample is first taken from a subject by an appropriate method. A target detection region is cloned into an appropriate vector and amplified through proliferation of a host cell (e.g., bacterial cell). Alternatively, DNA within the target detection region may be amplified by use of PCR. After the amplification, DNA within the target detection region is subjected to sequencing by an appropriate method. Examples of such a sequencing method include, but not limited to an automatic sequencing method. Examples of such an automatic sequencing method include a method using a Dye Terminator, and the like. The sequencing results are shown by an appropriate display method. Thereafter, the presence or absence of a predetermined mutation is determined.

(3) PCR Assay

In the present invention, a mutation of HTRA1 gene can be detected by use of an assay based on PCR. The PCR assay uses an oligonucleotide primer forming a hybrid only within a mutation type or wild type allele. A DNA sample is amplified by use of a primer set consisting of primers for a mutation type and a wild type. When only the mutation-type primer generates a PCR product, it is demonstrated that the subject has a mutation allele. When only the wild-type primer generates a PCR product, it is demonstrated that the subject has a wild-type allele.

RT-PCR can also be used to identify HTRA1 mRNAs. In RT-PCR, mRNA from the diseased tissue is converted into cDNA by the enzyme reverse transcriptase, using methods well-known to those of ordinary skill in the art. The entire coding sequence of the cDNA is then amplified via PCR using a forward primer located in the 3' untranslated region, and a reverse primer located in the 5' untranslated region. The amplified products can be analyzed, for example by comparing the size of the amplified products with the size of the expected product from normal mRNA, e.g., by agarose gel electrophoresis. Thereafter, the presence or absence of a predetermined mutation is determined.

(4) Hybridization Assay

In the present invention, a mutation of HTRA1 gene can be detected by hybridization assay. The hybridization assay is a method of determining the presence or absence of a predetermined mutation based on the ability of the DNA derived from a sample to hybridize with a complementary DNA molecule (e.g., oligonucleotide probe). Hybridization assay is performed by various hybridization techniques and detection techniques. Whether or not a probe hybridizes with a target detection sequence (e.g., mutation) can be directly detected by visualizing a hybridized probe. This method is known as Northern or Southern assay (Current Protocols in Molecular Biology, John Wiley & Sons, NY (1991)). Thereafter, the presence or absence of a predetermined mutation is determined.

2. Inhibition of Signaling by the TGF-β

(1) siRNA and shRNA

In order to inhibit the signaling by the TGF-β, a method is employed that inhibits expression and/or function of TGF-β. For inhibition of signaling by the TGF-β, RNA interference (RNAi) may be utilized. siRNA (small interfering RNA) targeting TGF-β gene can be designed and synthesized for transduction of cells for RNAi. RNAi is a phenomenon in which dsRNA (double-strand RNA) specifically and selectively binds to a target gene, which is subsequently removed to efficiently inhibit the expression of the target. For example, when dsRNA is introduced into a cell, expression of a gene having a homologous sequence to the RNA is knocked down. siRNA is designed as follows.

(a) There is no limitation to the gene as long as the gene codes for TGF-β or pro-TGF-β and any domains can be used as candidates. For example, in the case of human, any domains in GenBank Accession number NM_000660 (SEQ ID NO:3 and 4) can be used as candidates.

(b) From the selected domains, sequences starting with AA with a length of 19 to 25 bases, preferably 19 to 21 bases are selected. The GC contents of the sequences are, for example, conveniently 40-60%. siRNA can be introduced into a cell by a method in which siRNA synthesized in vitro is linked to plasmid DNA and then introduced into the cell or a method in which two RNAs are annealed.

According to the present invention, shRNA may be used for providing RNAi effect. shRNA is an RNA molecule called short hairpin RNA that has a stem-loop structure for forming a complementary strand between one domain and the other domain of the single-stranded molecule. shRNA can be designed such that a part thereof forms a stem-loop. For example, when sequence A represents a sequence of one domain and sequence B represents a sequence complementary to sequence A, sequence A, a spacer and sequence B are provided in this order in one RNA strand with the whole length being 45 to 60 bases. The target domain is not particularly limited and any domain can be a candidate.

(2) Decoy Nucleic Acid

A decoy nucleic acid in the present invention implies a short decoy nucleic acid including the binding site for a transcription factor. If this nucleic acid is transfected into the cell, transcription factor binds to this nucleic acid competitively to inhibit binding to the original binding site on the genome the transcription factor. As a result, expression of the transcription factor is inhibited. Typically, a decoy nucleic acid is a nucleic acid and its analogs, which contains at least one nucleic acid sequence that can bind to the target binding sequence. Decoy nucleic acids can be designed based on the nucleotide sequences of TGF-β or pro-TGF-β, by forming a single strand or double strands comprising of its complementary strand. The length is not particularly limited, but a desirable length ranges from 15 to 60 bases and preferably from 20 to 30 bases.

The siRNA, shRNA or decoy nucleic acid used in the present invention can be produced by a chemical synthesis or a biochemical synthesis known in the art. For example, a nucleic acid synthesis method using a common DNA/RNA synthesis device can be employed as a gene recombinant technology.

3. Pharmaceutical Composition Containing siRNA, shRNA or Decoy Nucleic Acid

The present invention relates to a pharmaceutical composition containing one or more said siRNA, shRNA or decoy nucleic acid for treating or preventing the cerebrovascular disease. Applicable diseases of the pharmaceutical composition of the present invention include CARASIL. When pharmaceutical composition of the present invention is applied to these diseases, said diseases can be present singly, or multiple diseases can be associated.

The pharmaceutical composition of the present invention can be used in such a form that siRNA, shRNA or decoy nucleic acids can be incorporated into the cellular lesions or into the tissue cells. The mode of administration of the pharmaceutical composition of the present invention can be either an oral or a parenteral route. In the case of oral administration, an appropriate drug form can be selected from tablets, pearls, sugarcoated tablets, capsules, liquid agents, gels, syrups, slurries and suspensions. In the case of parenteral administration, via pulmonary administration types (e.g., using a nebulizer, etc.), via nasal administration types, subcutaneous injection types (e.g., ointments, cream agents), and injection types are available. In the case of injection types, the pharmaceutical composition can be administered systemically or locally, directly or indirectly to the diseased areas via various drip fusions such as intravenous injection, intramuscular injection, intraperitoneal injection and subcutaneous injection.

When the pharmaceutical composition of the present invention is used as a gene therapy, in addition to direct administration by injection of the composition, a method of administering a vector incorporating the aforementioned siRNA, shRNA or decoy nucleic acid is available. As the aforementioned vectors, adenovirus vector, adeno-associated virus vector, herpes virus vector, vaccinia virus vector, retrovirus vector, lentivirus vector, and the like are available.

A pharmaceutical composition of the present invention can be introduced into a phospholipid vesicle, such as a liposome, and the vesicle can be administered. A vesicle retaining a pharmaceutical composition of the present invention is introduced into a specific cell by the lipofection method. The cells obtained are then administered systemically intravenously or intra-arterially. They can be administered locally, for example, to the brain, cerebral vessel, subarachnoid space or cerebral ventricle. In order to introduce the pharmaceutical composition of the present invention into the target tissues or organs, commercial gene transfection kits (e.g., Adeno Express: Clontech Corp.) can be used. As lipids to form a liposome structure, phospholipids, cholesterols and nitrolipids can be used.

The pharmaceutical composition of the present invention can be formulated by a conventional method and can contain pharmaceutically acceptable carriers. Such carriers can be additives or the following additives are available: water, pharmaceutically acceptable organic solvents, collagen, polyvinyl alcohol, polyvinylpyrrolidone, carboxyvinyl polymer, sodium carboxymethylcellulose, sodium polyacrylate, sodium alginate, water-soluble dextran, sodium carboxymethyl starch, pectin, methylcellulose, ethyl cellulose, xanthan gum, gum arabic, casein, agar, polyethylene glycol, diglycerin, glycerin, propylene glycol, vaseline, paraffin, stearyl alcohol, stearic acid, human serum albumin, mannitol, sorbitol, lactose, and surfactants that are acceptable as pharmaceutical additives.

The aforementioned additives can be selected singly or in combination according to the types of the pharmaceutical composition of the present invention. For example, when used as an injection formula, a purified nucleic acid is dissolved in a solvent (e.g., saline, buffer solution, glucose solution, etc.) and then mixed with Tween 80, Tween 20, gelatin, and human serum albumin, etc. Alternatively, it can be freeze-dried form to be dissolved before use. As an excipient for freeze dry, the following materials are available: sugars such as mannitol, glucose, lactose, sucrose, mannitol and sorbitol etc.; starch such as corn, wheat, rice, potato and other vegetable starch; celluloses such as methyl cellulose, hydroxypropylmethyl cellulose, or sodium carboxymethylcellulose; rubbers such as gum Arabic, traganto rubber; gelatin and collagen, etc. If desirable, disintegrants or solubilizers, such as cross-linked polyvinyl pyrrolidone, agar, alginic acid or its salts (e.g., sodium alginate) are available.

Doses of the pharmaceutical composition of the present invention vary with age, sex, symptoms, administration routes, frequency of administration, and types of formulas. A method of administration is appropriately selected based on patient's age and symptom. An effective dose is the amount of a nucleic acid that is required for reducing symptoms of the cerebrovascular diseases. A single dosage of the pharmaceutical composition of the present invention ranges from 0.1 µg to 100 mg per kg bodyweight and preferably from 1 to 10 µg. However, the aforementioned treatment agent is not limited by these dosages.

4. Kit

The term "kit" refers to a supply system for supplying primer set for amplifying wild type or mutated HTRA1 gene. When it is used in a reaction assay, a system for storing, transporting or supplying a reaction reagent and/or auxiliary substance is included in such a supply system. Examples of such a reaction reagent include, but not limited to, an oligonucleotide and an enzyme contained in a container. Examples of such an auxiliary substance include, but not limited to, a buffer and an instruction leaflet. Examples of such a kit include at least one type of accommodation unit (e.g., box) containing a relevant reaction reagent and/or auxiliary substance, and the like.

EXAMPLES

Hereinbelow, the present invention will be described more specifically with reference to the following Example. However, the technical scope of the present invention is not limited to the Example.

Methods

Subjects and Genetic Analysis

We enrolled five probands of consanguineous families of Asian (Japanese) ancestral origin and some of their family members for linkage analysis (families 2285, 1872, 2321, 2402, and 2520 in Table 1 and FIG. 1A). After identification of the causative gene for CARASIL, we enrolled one additional subject in family 3119 with pathologically confirmed CARASIL (Table 1). On neuropathological examination in the patient in family 3119, arteriosclerosis associated with intimal thickening and dense collagen fibers was observed in cerebral small arteries (FIG. 1I). Ancestry was determined by self-report form the participant or family members. Probands showed diffuse white matter lesions on magnetic resonance imaging, autosomal recessive inheritance, onset of symptoms between their second and fifth decade, and spondylosis or alopecia (Table 1 and FIGS. 1E, 1F, 1G, and 1H).[6-8]

TABLE 1

Clinical Features of the Six Patients with CARASIL

| Clinical Features | II-2 2285 | II-3 1872 | II-1 3119 | II-7 2321 | II-3 2404 | II-3 2520 | No./Total |
|---|---|---|---|---|---|---|---|
| Consanguinity | + | + | + | + | + | + | |
| Mutation | C1108→T R370X | C904→T R302X | C904→T R302X | G889→A V297M | G889→A V297M | G754→A A252T | |
| Sex | F | M | F | F | M | F | |
| Age at time of study (yr) | 44 | 28 | 46 | 50 | 33 | 48 | |
| Age at onset (yr) | 18 | 16 | 14 | 16 | 14 | Teens | |
| Initial symptom | Alopecia | Alopecia | Alopecia | Alopecia | Alopecia | Lumbago | |
| Leukoaraiosis on brain magnetic resonance imaging | + | + | + | + | + | + | 6/6 |
| Alopecia (yr) | + (18) | + (16) | + (14) | + (16) | + (14) | − | 5/6 |
| Spondylosis (yr) | + (21) | + (21) | + (29) | + (39) | + (33) | + (teens) | 6/6 |

TABLE 1-continued

Clinical Features of the Six Patients with CARASIL

| Clinical Features | Patient and Pedigree No. | | | | | | No./Total |
|---|---|---|---|---|---|---|---|
| | II-2 2285 | II-3 1872 | II-1 3119 | II-7 2321 | II-3 2404 | II-3 2520 | |
| Dementia (yr) | + (35) | + (37) | + (29) | + (50) | + (33) | − | 5/6 |
| Acute stroke (yr) | − | + (31) | − | − | − | + (38) | 2/6 |
| Gait disturbance (yr) | + (35) | + (26) | + (32) | + (31) | + (29) | + (38) | 6/6 |
| Pseudobulbar palsy (yr) | + (35) | + (26) | + (32) | + (50) | + (33) | + (38) | 6/6 |
| Pyramidal sign (yr) | + (35) | + (27) | + (32) | + (50) | + (29) | + (48) | 6/6 |
| Hypertension | − | − | − | − | − | − | 0/6 |

The numbers in parentheses refer to the age at onset for each symptom. None of the patients had any malignancy, abnormalities in the retinal artery, or macular degeneration.

Although the affected persons of family 2520 did not have alopecia and cognitive impairment, we enrolled this family because the patients had diffuse white matter lesions on magnetic resonance imaging and spondylosis, and an affected sibling had pathological findings identical to those of CARASIL.[8] We isolated genomic DNA from eleven subjects, including the five probands from these five families with CARASIL. We performed a genomewide linkage analysis using 763 microsatellite markers (Applied Biosystems). Pairwise logarithm of the odds (LOD) scores were calculated with the MLINK program of the LINKAGE 5.2 and FASTLINK 4.1P package.[12, 13] We established five new microsatellite markers, namely, M1236, M1238, M1241, M1260, and M1264, on the basis of simple-repeat information from the UCSC Genome Browser on Human. Primer sequences of these markers are summarized in Table 2.
Primer Sequences for Originally Established Polymorphic Markers.

To narrow the candidate interval, we established five new microsatellite markers, namely, M1236, M1238, M1241, M1260, and M1264, based on simple repeat information obtained from the 2006 human reference sequence in the University of California Santa Cruz Genome Browser Database (http://genome.ucsc.edu/index.html).

The following table 2 is a summary of amplification primers for the markers.

TABLE 2

| Marker | Forward Primer Reverse Primer | SEQ ID NO SEQ ID NO | Start position on chromosome 10 |
|---|---|---|---|
| M1236 | ATTACAGGCATGAGCCACTG TTGTCTGCCATACATGCTGC | 5 6 | 124,022,184 |
| M1238 | GGGAACTAAGAGATGCTGAG TGTTGCTACCTTTTGCATCTC | 7 8 | 124,148,100 |
| M1241 | AAAACTAGGCTTGCCCACAAG AGGGTGCCACTTGCTATTTG | 9 10 | 124,567,939 |
| M1260 | ACGAGACAAGACTTCTTTCAG CCACAGTAGTAACCTCTTTAG | 11 12 | 126,435,697 |
| M1264 | AAAATTACCGGGCACATTCAC CTCATGATACGTTAAGGGAAG | 13 14 | 126,863,922 |

We designed primer pairs for amplification of the nine coding exons of HTRA1. Control subjects to provide DNA and fibroblasts were recruited from healthy individuals of Asian (Japanese) ancestral origin, as determined by self-report. Control subjects were between 74 and 90 years of age, with no signs of dementia, as defined by the minimental state examination. We obtained written informed consent from the affected persons and their family members and written and oral informed consent from the control persons. The institutional review board of Niigata University approved this study.

Assay of HTRA1 Protease Activity

We subcloned wild-type or mutant HTRA1 complementary DNA (cDNA) lacking 1-140 codons into the vector pGEX 6P-3 to express polypeptides in *Escherichia coli* as fusions with glutathione S-transferase (GST) (GE Healthcare). Amino acid substitution of the serine protease motif S328A, which abolishes the protease activity in HTRA1, was used as a negative control.[14] GST fusion proteins were overexpressed and purified. Protease activity using FITC-labeled substrate β-casein was evaluated with a Quanti-Cleave Fluorescent Protease Assay Kit (Pierce) by using recombinant GST-HTRA1. To eliminate the possibility that the lack of an N-terminus for GST-HTRA1 affects the result of protease activity, we also performed the identical protease assay using the conditioned media from cells stably expressing full-length wild-type or mutant HTRA1 tagged with a green fluorescent protein (GFP). GFP-tagged HTRA1 proteins were detected by using anti-GFP antibody (MBL).

To assay formation of a stable complex with α1-antitrypsin, we transiently expressed α1-antitrypsin and either wild-type or mutated HTRA1 cDNAs with a V5 tag at the C-terminus in HEK293 cells. These cells were grown in serum-free medium, and conditioned media were then immunoblotted with anti-V5 antibody.[14]

Expression of HTRA1 and NOG mRNA

Total RNA was isolated from whole blood or cultured skin fibroblasts. cDNA was synthesized with the High-Capacity cDNA Reverse Transcription kit (Applied Biosystems). We assayed the expression of HTRA1 mRNA in whole blood using gene-specific primers for HTRA1. To assay HTRA1 mRNA levels in cultured skin fibroblasts in relation to the expression of glyceraldehyde 3-phosphate dehydrogenase, we performed real-time quantitative reverse transcription-polymerase chain reaction (RT-PCR) using specific Taq-Man® probes and primer sets (Applied Biosystems). We assayed NOG mRNA levels in cultured skin fibroblasts in relation to the expression of β-actin by real-time quantitative RT-PCR using SYBR Green assay (Applied Biosystems).

Reverse Transcription-Polymerase Chain Reaction Assay to Amplify HTRA1 and NOG mRNA.

To determine whether R370X nonsense mutation in HTRA1 resulted in loss of mRNA from a mutant allele, we analyzed mRNA from whole blood. Total RNA was isolated with the PAX Gene Blood RNA kit (Pre-Analytix). cDNA was synthesized with the High-Capacity cDNA Reverse Transcription kit (Applied Biosystems). PCR was performed with the following primer pair.

```
                                        (SEQ ID NO: 15)
   Forward primer: 5'-CGCCATCATCAACTATCG-3'

(SEQ ID NO: 16)
   Reverse primer: 5'-GTCAAAAGTCTTGAGTGTCC-3'
```

RT-PCR products were analyzed on a 2% agarose gel and sequenced with the use of the same primers.

To quantify HTRA1 mRNA levels in cultured skin fibroblasts, we performed real-time RT-PCR using TaqMan® Gene expression assays (Applied Biosystems) (Hs01016151 m1 for HTRA1 and Hs99999905 m1 for glyceraldehyde 3-phosphate dehydrogenase as a control). Real-time RT-PCR amplification was carried out on an ABI Prism 7100 Sequence Detection System (Applied Biosystems). To quantify NOG mRNA levels in cultured skin fibroblasts in relation to the β-actin mRNA levels as control, the following primer pairs were designed.

```
   For NOG mRNA
                                        (SEQ ID NO: 17)
   Forward primer: 5'-CCAGCACTATCTCCACATC-3'

(SEQ ID NO: 18)
   Reverse primer: 5'-GCAGCGTCTCGTTCAGATC-3'

For β-actin mRNA
                                        (SEQ ID NO: 19)
   Forward primer: 5'-CTTCTACAATGAGCTGCGTG-3'

(SEQ ID NO: 20)
   Reverse primer: 5'-GTCTCAAACATGATCTGGGTC-3'
```

Assay of Signaling by TGF-β Family Proteins

We used GeneTailor site-directed mutagenesis system (Invitrogen) to synthesize cDNA encoding HTRA1 mutants and constitutively active TGF-β1 proprotein (pro-TGF-β1 containing the activating mutations C223S/C225S)[17] and then individually subcloned these cDNAs into the pcDNA DEST-40 vector (Invitrogen). Constitutively active TGF-β1 was synthesized from pro-TGF-β1 containing the activating mutations C223S/C225S. We isolated SMAD2 cDNA from a human whole-brain cDNA library (Clontech) and subcloned it into the pcDNA DEST-40 vector. Luciferase assays were performed as previously described.[15,16] Mouse C2C12 myoblasts were cotransfected with pRL-TK renilla luciferase expression plasmid, HTRA1 expression vectors, and the following constructs: (SBE)[4]-firefly luciferase vector (TGF-β responsive reporter vector) and vectors containing SMAD2, SMAD4, and TGF-β1 (encoding pro-TGF-β1 with two point mutations (C223S, C225S));[17] pGL3-Id985WT-firefly luciferase vector (BMP responsive reporter vector)[16] and vectors containing SMAD1, SMAD4, and BMP-4 (encoding pro-bone morphogenetic protein 4); pGL3-Id985WT-firefly luciferase vector (BMP responsive reporter vector)[16] and vectors containing SMAD1, SMAD4, and BMP-2 (encoding pro-BMP-2).[18] Cell extracts were assayed for luciferase activity with the use of the Dual-Luciferase Reporter Assay System (Promega). The activity was corrected for transfection efficiency by using pRL-TK renilla luciferase activity. Every sample was transfected in triplicate, and every experiment was repeated three times.

Phosphorylation of Smad Proteins

Human embryonic kidney (HEK) 293 cells were cotransfected with vectors containing HTRA1 and the following constructs: vectors containing SMAD2, SMAD4, and TGF-β1 (encoding pro-TGFβ1 with two point mutations (C223S, C225S)); vectors containing SMAD1, SMAD4, and BMP-4; vectors containing SMAD1, SMAD4, and BMP-2.[17,18] The cells were lysed in RIPA buffer containing phosphatase inhibitor. We detected Smad1, phosphorylated Smad1, Smad2, and phosphorylated Smad2 proteins using anti-Smad1, anti-phospho-Smad1/5/8, anti-Smad2/3, and anti-phospho-Smad2 (Cell Signaling) antibodies, respectively, through analysis by Western blot.

Immunohistochemistry and In Situ Hybridization.

We carried out immunoperoxidase staining on formalin-fixed, paraffin-embedded brains, obtained from two autopsied patients with CARASIL or autopsied control subjects (84-year-old female person with stroke, a person with schizophrenia, and a person with amyotrophic lateral sclerosis).[8,9] The primary antibodies were against TGF-β1 (1:50, Santa Cruz), versican (1:100, Seikagaku), and fibronectin ED-A (1:100, Abcam). Nonimmune immunoglobulin G was used as a negative control. We used cDNA encoding the ED-A domain of fibronectin (5404-5704 nucleotide fragment of fibronectin isoform 1: NM_212482.1) as a template for digoxigenin-labeled antisense and sense-complementary RNA probes. The sense probe was used as a negative control. We carried out in situ hybridization on the paraffin-embedded sections with the probes. After washing and blocking procedures, the sections were incubated with alkaline phosphatase-conjugated anti-digoxigenin antibodies. The signal was developed in 4-nitroblue tetrazolium chloride/5-bromo-4-chloro-3-indolyl phosphate solution (Roche). The sections were counterstained with Fast Red.

Results

Genetic Analysis

On carrying out genomewide linkage analysis of the five families, we obtained maximal cumulative pairwise LOD scores of 3.97 and 3.59 at D10S587 and D10S1656 (θ=0.0); these markers were homozygous in all patients (FIG. 1A). We then fine-mapped the region between D10S597 and D10S575 using D10S1483 and five established polymorphic microsatellite markers (M1236, M1238, M1241, M1260, and M1264 see Table 2) (FIGS. 1A and 1B). The region between M1236 and M1260 was homozygous in all probands, suggesting that the causative gene was located within this 2.4-Mb region.

We first selected HTRA1 as a candidate (FIG. 1B), because it is expressed in the blood vessels, skin, and bone.[19] We identified two homozygous nonsense mutations: C1108→T (resulting in a stop codon at 370: R370X) in family 2285 and C904→T (resulting in a stop codon at 302: R302X) in family 1872 (FIG. 1C). We also identified two homozygous missense mutations: G889→A (predicted to result in the amino acid substitution V297M) in families 2321 and 2404, and G754→A (predicted to result in the amino acid substitution A252T) in family 2520. In addition, we observed a homozygous nonsense mutation C904→T in the proband of family 3119. The missense mutations V297M and A252T were located in the genic region encoding the serine protease domain, and the amino acids predicted to be affected are either absolutely or strongly conserved among the HTRA homologues and HTRA1 orthologues (FIGS. 1C and 1D). We did not observe these changes in the 125 control persons.

Protease Activity of Mutant HTRA1

The protease activities of the HTRA1 encoded by constructs containing either of the missense mutations or of R370X were 21-50% of the activity of wild-type HTRA1. In contrast, HTRA1 encoded by a construct containing the R370X mutation had a protease activity similar to that of wild-type HTRA1 (FIGS. 2A and B). HTRA1 attacks the reactive center loop of α1-antitrypsin, instigating serine protease activity of α1-antitrypsin which thereby mediates the formation of a covalent complex between the two molecules.[14] We did not observe the formation of a stable complex between α1-antitrypsin and the mutant HTRA1s encoded by cDNAs containing either V297M, A252T, or R302X. In contrast, wild-type HTRA1, and that encoded by a cDNA containing R370X formed stable complexes with a1-antitrypsin (FIG. 2C).

Nonsense-Medicated Decay

When a premature stop codon is located at least 50 to 55 nucleotides upstream of the 3'-most exon-exon junction, messenger RNAs (mRNAs) may be degraded by nonsense-mediated decay.[20] Because the location of R370X fulfills these criteria (FIG. 1C), we determined whether R370X-containing HTRA1 mRNA is degraded by nonsense-mediated decay. The level of HTRA1 mRNA expression in fibroblasts from the patient with the R370X mutation is 6.0% of that of control subjects, and treatment with cycloheximide, an inhibitor of nonsense-mediated decay, increased expression of R370X HTRA1 mRNA to four times to that of the basal level (FIG. 3A). We did not detect HTRA1 protein in the culture medium of fibroblasts from the patient carrying the R370X mutation (FIG. 3B). Furthermore, analysis of HTRA1 of leukocytes from a heterozygous carrier of this mutation showed the presence of wild-type HTRA1 mRNA only (FIG. 3C).

Mutant HTRA1 and Signaling by TGF-β Homologues.

Figure 4:
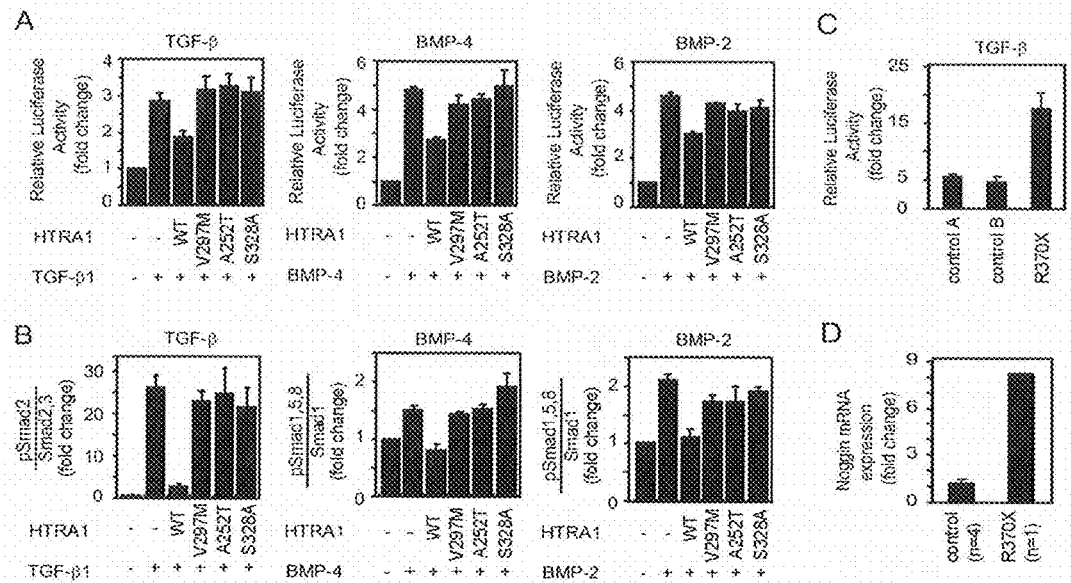
FIG. 4. Modulation of TGF-β Family-Mediated Transcriptional Responses by Mutated HTRA1 Proteins.
Figure 4:
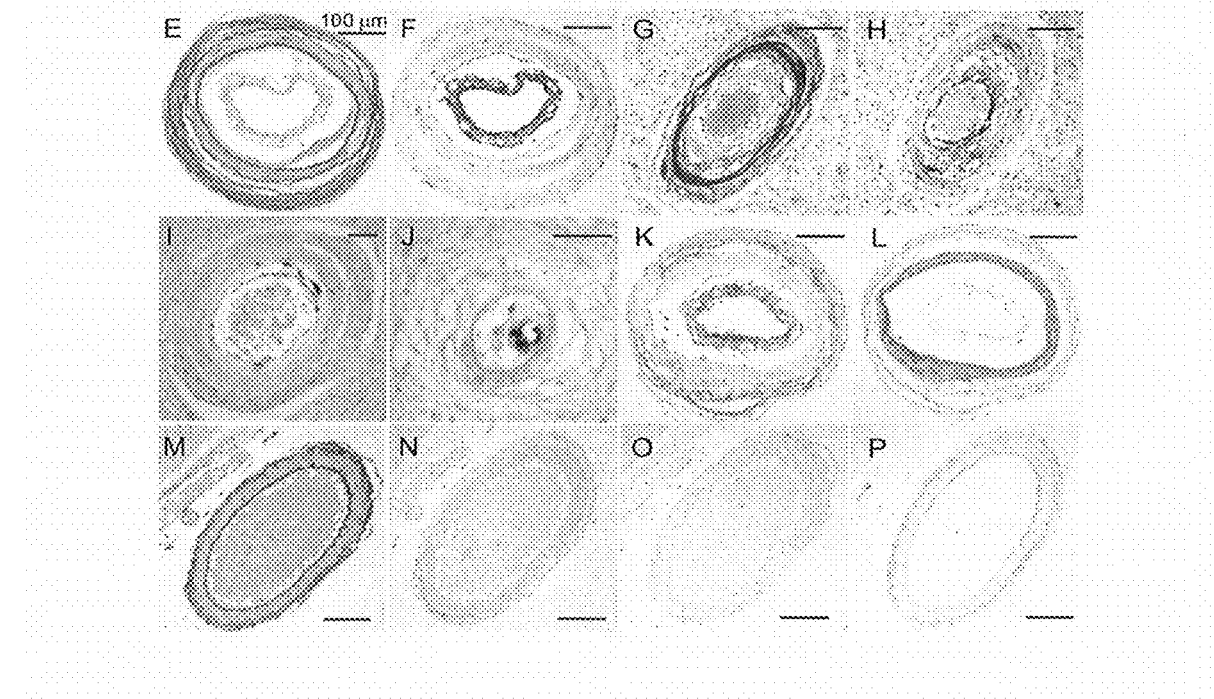
Figure 5:
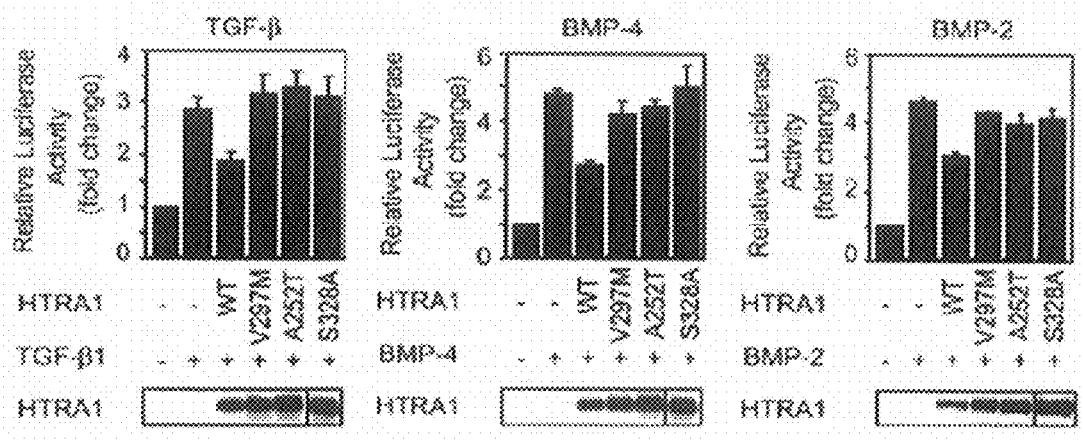
FIG. 5. Expression Level of Transfected HTRA1 Proteins in TGF-β Family-Mediated Transcriptional Response Assay.
Figure 6:
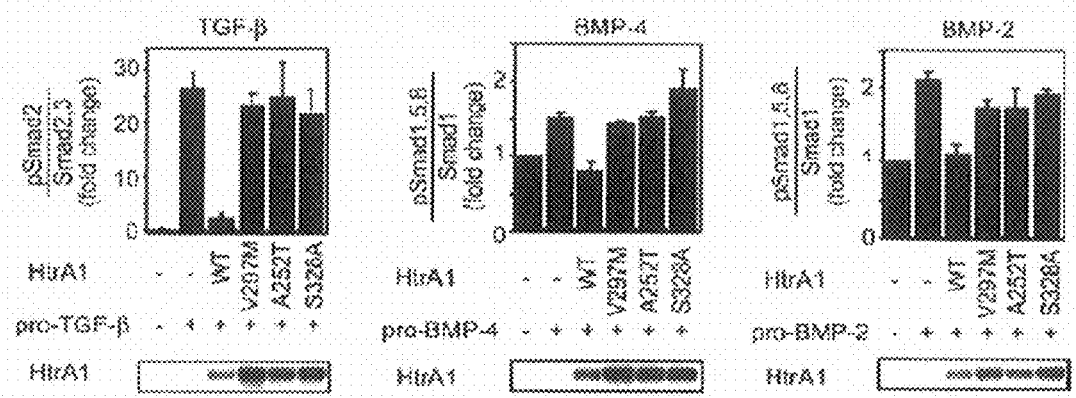
FIG. 6. Expression Level of Transfected HTRA1 Proteins in Assay of Phosphorylation of Smad proteins.

The serine protease activity of HTRA1 is necessary for the inhibition of TGF-β family signaling.[15] We therefore tested the ability of mutant variants of HTRA1 with "missense" amino acids to repress signaling by the TGF-β family members TGF-β, BMP-4 and BMP-2 (FIG. 4A and FIG. 5). As expected, none of the missense-mutated HTRA1 proteins repressed signaling by these molecules. To exclude the possibility that HTRA1 protease activity directly affects the reporter system, we assayed the phosphorylation of Smad in these assays (phosphorylated Smad is a downstream effector of the TGF-β family signaling pathway), and observed that none of the mutant HTRA1 proteins repressed the subsequent phosphorylation of Smad proteins (FIG. 4B and FIG. 6).

Figure 7:
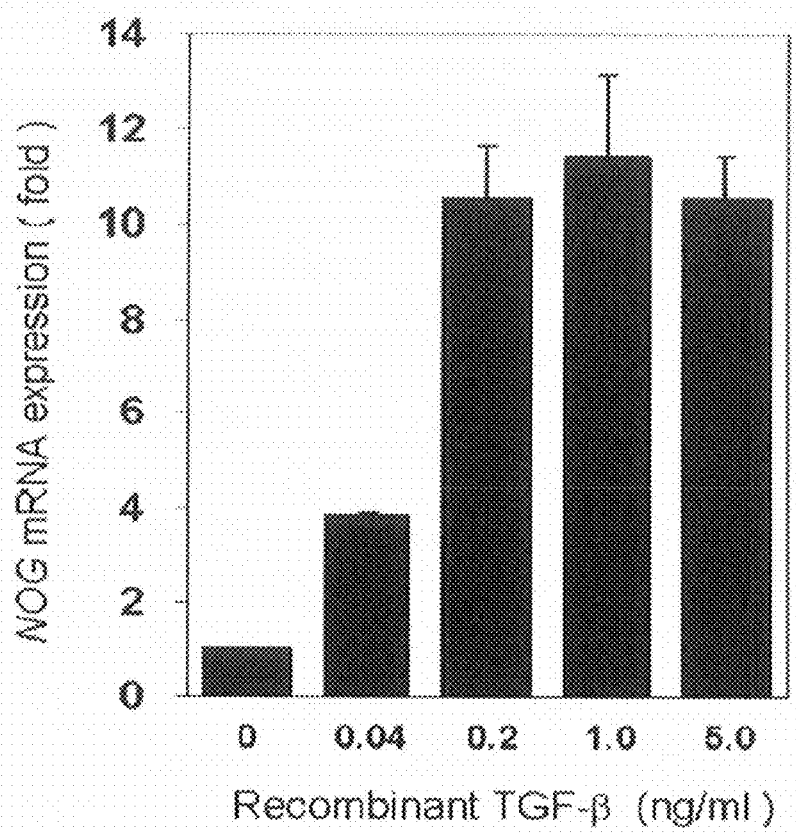
FIG. 7. Effects of TGF-β on NOG mRNA Expression in Cultured Skin Fibroblasts.

We next investigated TGF-β signaling in fibroblasts from the subject with CARASIL with the R370X mutation and observed that the TGF-β signaling in these fibroblasts was more than three times that of control subjects (FIG. 4C). In addition, NOG mRNA, which is induced by TGF-β signaling in fibroblasts, was also elevated in the probands (FIG. 4D and FIG. 7).[21]

Figure 8:
FIG. 8 Immunohistochemical Analysis in Cerebral Small Arteries.
Figure 9:
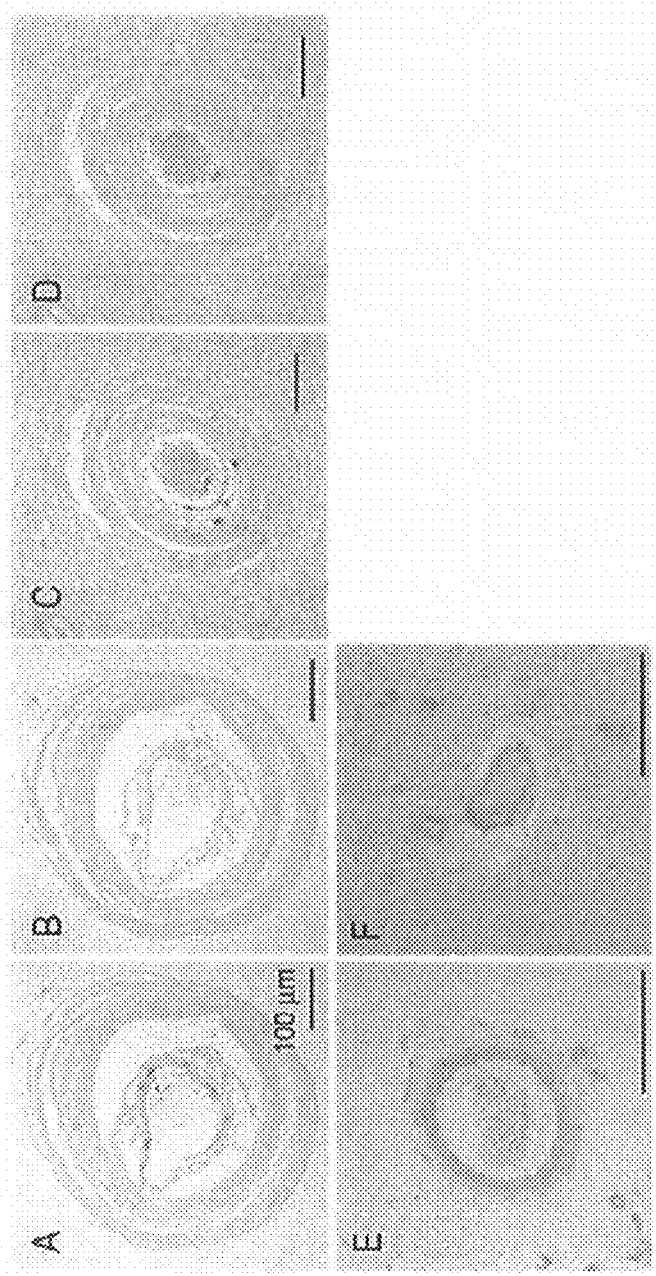
FIG. 9. mRNA Expression of Extra Domain-A of Fibronectin in Cerebral Small Arteries.

Increased TGF-β signaling results in vascular fibrosis, with synthesis of extracellular matrix proteins including ED-A fibronectin and versican.[22-24] The intima of the CARASIL patients carrying the R302X or A252T mutation showed increased expression of ED-A fibronectin (FIG. 4E, 4F, 4G, 4H, and FIG. 8) and versican (FIG. 4K and FIG. 8) when compared with those of control subjects (FIGS. 4M, N and 4O). The result was confirmed by an in situ hybridization assay that used a probe for ED-A fibronectin (FIG. 4I, 4J and FIG. 9). Moreover, the media of CARASIL patients exhibited elevated expression of TGF-β1 (FIG. 4L, 4P and FIG. 8). These results indicate increased TGF-β signaling in the cerebral small arteries in CARASIL.

Discussion

TGF-β family signaling is tightly associated with vascular angiogenesis and remodeling and has multifaceted roles in vascular endothelial cells and vascular smooth muscle cells, depending on the cell types and extracellular matrix.[25, 26] Moreover, dysregulation of TGF-β family signaling results in hereditary vascular disorders.[26] Defective TGF-β signaling by mutations in the TGF-β receptors leads to hereditary hemorrhagic telangiectasia, whereas activation of TGF-β signaling contributes to Marfan syndrome and associated disorders.[26] Our findings extend the spectrum of diseases shown to be caused by the dysregulation of TGF-β signaling to include hereditary ischemic cerebral small-vessel disease. In addition, the pathological findings in CARASIL resemble those observed in nonhereditary ischemic cerebral small-vessel disease with hypertension; hypertension may increase TGF-β signaling.[7-11, 27] Thus, TGF-β signaling might underlie the molecular basis of nonhereditary ischemic cerebral small-vessel disease with hypertension.

Disregulation of inhibition of TGF-β family signaling also has been linked to alopecia and spondylosis, the other cardinal clinical features of CARASIL. Transgenic mice overexpressing BMP-4, BMP-2, and TGF-β exhibit hair loss or retardation of the development of hair follicles.[28, 29] BMP family members are well-known regulators of bone formation, repair, and regeneration.[30] Furthermore, HTRA1 overexpression decreases BMP-2-induced mineralization, whereas reduced expression of HTRA1 accelerates mineralization.[31] Although it is possible that the loss of protease activity by HTRA1 on other substrates associates with the pathogenesis of CARASIL, these findings strengthen the hypothesis that increased TGF-β family signaling contributes to the pathogenesis of CARASIL.[14, 31-33] It remains unclear why disinhibition of signaling by TGF-β family members caused by mutant HTRA1 results in narrowly-restricted clinical phenotypes. Tissue-specific regulation of TGF-β family signaling or tissue-specific expression of HTRA1 is an explanation.[14, 33, 34 25, 26]

The molecular basis for regulation of TGF-β1 signaling by HTRA1 remains to be elucidated.[15, 35, 36] TGF-β1 is synthesized as a proprotein (pro-TGF-β1) and is subsequently cleaved into latency associated protein (LAP) and mature TGF-β1 by proprotein convertase.[26] The mature TGF-β1 is non-covalently bound to LAP and is sequestrated as a LAP-TGF-β1 complex in an extracellular matrix.[26] The mature TGF-β1 is released from the LAP-TGF-β1 complex and is presented. Thus the TGF-β1 signaling is regulated by balancing between maturation, sequestration, and presentation. Interestingly, Emilin1 inhibits TGF-β1 signaling by preventing the processing of pro-TGF-β1 into mature TGF-β1.[37] The CARASIL patients demonstrated increased expression of mature TGF-β1, suggesting that the HTRA1 might also prevent the processing of pro-TGF-β1 into mature TGF-β1 depending on its protease activity. A single nucleotide polymorphism in the promoter region of HTRA1, which is associated with elevated expression levels of HTRA1, is a genetic risk factor for the neovascular form of age-related macular degeneration (AMD).[38, 39] We observed no macular degeneration in the persons with CARASIL, consistent with the hypothesis that increased expression of HTRA1 contributes to age-related macular degeneration.[6-8, 38] That said, all of our patients were younger than the typical age of onset of neovascular form of AMD.

Our results indicate that dysinhibition of TGF-β family signaling underlies the molecular basis for CARASIL and provide a basis for further investigation of therapeutic strategies for ischemic cerebral small-vessel disease, alopecia, and spondylosis.

Figure Legends

FIG. 1. Pedigrees and HTRA1 Mutations of Families with CARASIL.

Panel A shows pedigrees of families with CARASIL. Squares denote men; circles, women; solid symbols, affected family members; open symbols, unaffected members; double horizontal lines, consanguineous marriage. Microsatellite markers are shown in order from the centromere to the q-arm terminus. Originally developed microsatellite markers are indicated in blue type. Alleles where the phases are unequivocally determined are shown in parentheses. The region of homozygosity for each affected subject is boxed. Panel B shows the physical map of the candidate region for CARASIL on chromosome 10q. Panel C shows the distribution of mutations in HTRA1, which consists of nine exons (squares). Colored boxes represent exons corresponding to the insulin-like growth factor binding protein domain (green), Kazal-type serine protease inhibitor domain (red), trypsin-like serine protease domain (blue), PDZ domain (yellow), and untranslated regions (gray). The missense mutations are in black type, and the nonsense mutations are in red type. Panel D shows the conservation of HTRA1 residues mutated in CARASIL. Conserved amino-acid residues are shaded (black, 100%; dark gray, 80%; gray, 60%). Sequences were obtained from GeneBank. T2-weighted magnetic resonance imaging of the brain (repetition time, 5000 msec; echo time, 150 msec) with a thickness of 5 mm showed an ischemic region in the basal ganglia and white matter (panels E and F; subject family 2321), and T1-weighted lumbar magnetic resonance imaging (repetition time, 519 msec; echo time, 19 msec) with a thickness of 5 mm showed spondylotic changes of the lumbar spine (panel G; subject II-3, family 1872). Diffuse hair loss in the temporal and/or parietal area of the head was observed (subject II-2, family 2285; panel H). Cerebral small arteries in the arachnoid from subject II-1, family 3119, showed marked intimal thickening, narrowing of the lumen, hyalinosis, and splitting of the internal elastic membrane (panel I, elastica van Gieson stain).

Figure 2:
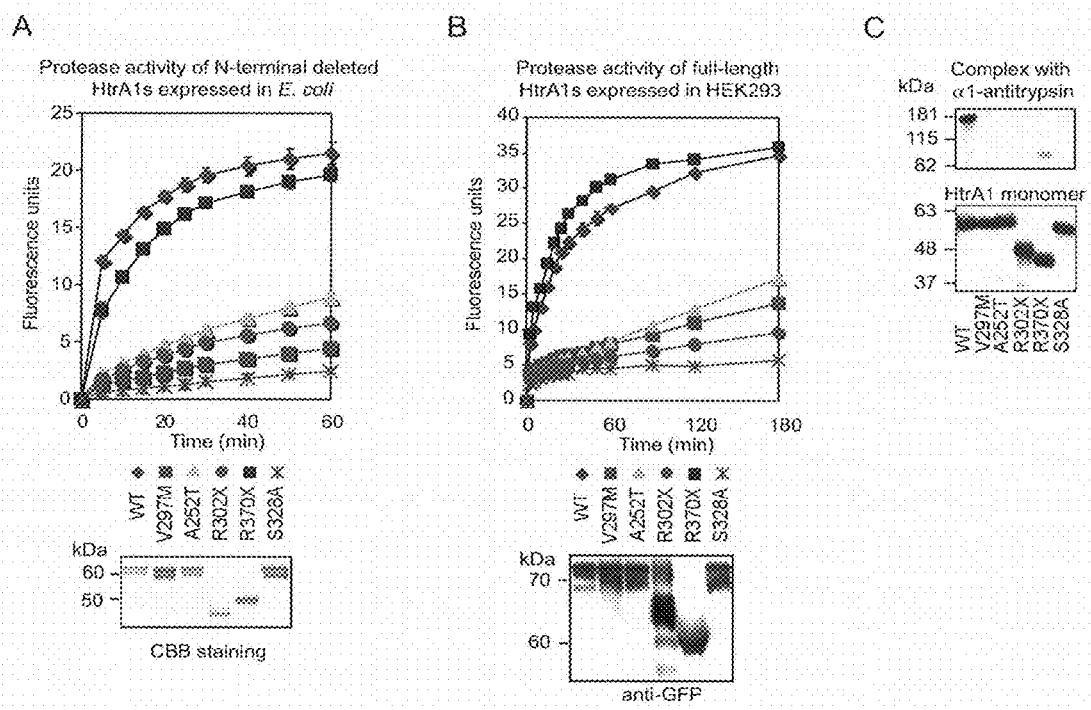
FIG. 2. Functional Consequences of HTRA1 Mutations in CARASIL.

FIG. 2. Functional Consequences of HTRA1 Mutations in CARASIL.

Panels A and B show FITC-labeled β-casein assay of mutated HTRA1s. The fluorescence units represent the protease activity. Conditioned media from HEK293 cells that stably expressed HTRA1s tagged with a green fluorescent protein (GFP) at the C-terminus (panel A) or recombinant N-terminal deleted HTRA1 proteins expressed in *E. coli* (panel B) were incubated with FITC-labeled β-casein. The amount of HTRA1 proteins was shown by immunoblotting with an anti-GFP antibody (panel A) or Coomassie brilliant blue (CBB) staining (panel B). The bars represent standard errors. Panel C shows a covalent complex formation (high molecular weight products; upper panel) between al-antitrypsin and either wild-type (WT) or R370X HTRA1. Formation of the stable HtrA/α1-antitrypsin complex does not occur in the other mutant HTRA1s. The amount of HTRA1 proteins was shown by immunoblotting with an anti-V5 antibody (lower panel).

Figure 3:
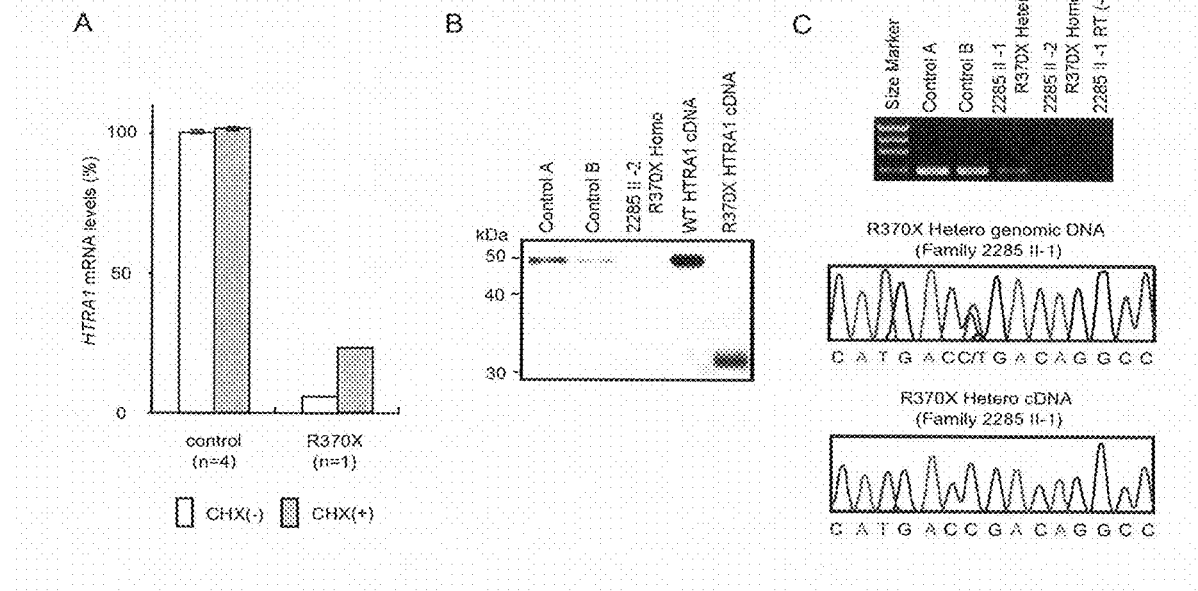
FIG. 3. Nonsense-Mediated Decay of Nonsense-Mutated HTRA1 mRNA.

FIG. 3. Nonsense-Mediated Decay of Nonsense-Mutated HTRA1 mRNA.

Panel A shows HTRA1 mRNA levels in cultured skin fibroblasts from subject II-2, family 2285, with R370X HTRA1 as a percentage of levels in cells from control subjects (n=4) with or without the nonsense-mediated decay inhibitor cycloheximide (CHX; 100 μg/m) for 4 h. The bars represent the standard errors. Panel B shows Western blot analysis of HTRA1 using the cultured skin fibroblasts of subject II-2, family 2285, with R370X and control subject with HTRA1 antibody (MAB2916; R&D Systems). Panel C shows the results of RT-PCR assay. HTRA1 PCR amplicons, the expected transcripts length of 600 bp, were obtained from cDNA prepared from peripheral blood of the heterozygote II-1, family 2285, whereas they were not obtained from cDNA prepared from peripheral blood of subject II-2, family 2285. Electrophoregrams show wild-type and mutant (C1108→T) alleles in the PCR products derived from the genomic DNA of the leukocytes of the unaffected heterozygous subject II-1, family 2285, whereas only wild-type allele was detected in the reverse transcription PCR products derived from the RNA of the leukocytes of the same individual.

FIG. 4. Modulation of TGF-β Family-Mediated Transcriptional Responses by Mutated HTRA1 Proteins.

In Panel A, C2C12 cells were cotransfected with pRL-TK renilla luciferase expression plasmid, wildtype (WT) or mutated HTRA1 expression plasmid, and the following constructs: (left) (SBE)$^4$-firefly luciferase vector (TGF-β responsive reporter vector) and vectors containing SMAD2, SMAD4, and TGF-β1 (encoding pro-TGF-β1 with two point mutations C223S/C225S);[17] (middle) pGL3-Id985WT-firefly luciferase vector (BMP responsive reporter vector)[16] and vectors containing SMAD1, SMAD4, and BMP-4 (encoding pro-bone morphogenetic protein 4); (right) pGL3-Id985WT-firefly luciferase vector (BMP responsive reporter vector)[16] and vectors containing SMAD1, SMAD4, and BMP-2 (encoding pro-BMP-2).[18] Data represent the mean with standard error of normalized firefly luciferase/renilla luciferase activities from three independent experiments. In Panel B, HEK293 cells were cotransfected with WT or mutated HTRA1-V5 expression vectors the following constructs: (left) vectors containing SMAD2, SMAD4, and TGF-β1 (encoding pro-TGF-β1 with two point mutations (C223S, C225S));[17] (middle) vectors containing SMAD1, SMAD4, and BMP-4 (encoding pro-bone morphogenetic protein 4); vectors containing SMAD1, SMAD4, and BMP-2 (encoding pro-BMP-2).[18] The ratio of phosphorylated Smad proteins was examined by immunoblotting of whole-cell lysates. Data represent the mean with standard error of four independent experiments. In panels A and B, the mean values for WT-HTRA1 are significantly lower than others by the Tukey's multiple-comparison test (P<0.05). In panel C, fibroblasts from two control subjects and subject II-2, family 2285, with R370X HTRA1 were cotransfected with pRL-TK renilla luciferase expression plasmid and vectors containing SMAD2, SMAD4, and TGF-β1 (encoding pro-TGF-β1 with two point mutations (C2235, C225S)).[17] The mean values for R370X are significantly higher than others by the Tukey's multiple-comparison test (P<0.05). Panel D shows NOG mRNA levels in fibroblasts from subject II-2, family 2285, with R370X HTRA1 as a ratio of levels in fibroblasts from control subjects (n=4). In panels E, F, G, H, I, J, K, and L, small cerebral arteries of autopsied subject II-1, family 3119 (homozygous for the R302X mutation) shows marked intimal proliferation (panels E and G, elastica van Gieson stain), increased expression of an ED-A fibronectin in intima (panels F and H, IST-9 antibody), increased mRNA expression of an ED-A fibronectin in endothelial cells and subendothelial smooth muscle cells (panels I and J), and increased expression of a versican in intima (panel K) and TGF-β1 in media (panel L). In panels M, N, O, and P, immunohistochemical analysis in the cerebral small arteries from autopsied control subject (40-year-old female with amyotrophic lateral sclerosis). Elastica van Gieson stain (panel M) and staining with anti-EDA-fibronectin antibody (IST-9: panel N), anti-versican antibody (panel O) and anti-TGF-β1 antibody (panel P). The same results were obtained from two additional control subjects (84-year-old female, 62-year-old male with stroke, and 36-year-old female with schizophrenia).

FIG. 5

Expression Level of Transfected HTRA1 Proteins in TGF-β Family-Mediated Transcriptional Response Assay.

C2C12 cells were cotransfected with pRL-TK renilla luciferase expression plasmid, wild-type (WT) or mutated HTRA1 expression plasmid, and the following constructs:

(Left) (SBE)$_4$-firefly luciferase vector (TGF-β responsive reporter vector) and vectors containing SMAD2, SMAD4, and TGF-β1 (encoding pro-TGF-β1 with two point mutations C223S/C225S);

(Middle) pGL3-Id985WT-firefly luciferase vector (BMP responsive reporter vector) and vectors containing SMAD1, SMAD4, and BMP-4 (encoding pro-bone morphogenetic protein 4);

(Right) pGL3-Id985WT-firefly luciferase vector (BMP responsive reporter vector) and vectors containing SMAD1, SMAD4, and BMP-2 (encoding pro-BMP-2).

Data represent the mean with standard error of normalized firefly luciferase/renilla luciferase activities from three independent experiments (top panel). The HTRA1 proteins were stained with anti-V5 antibody (bottom panel).

FIG. 6

Expression Level of Transfected HTRA1 Proteins in Assay of Phosphorylation of Smad Proteins.

HEK293 cells were cotransfected with WT or mutated HTRA1-V5 expression vectors, and the following constructs:

(Left) vectors containing SMAD2, SMAD4, and TGF-β1 (encoding pro-TGF-β1 with two point mutations C223S/C225S);

(Middle) vectors containing SMAD1, SMAD4, and BMP-4 (encoding pro-bone morphogenetic protein 4);

(Right) vectors containing SMAD1, SMAD4, and BMP-2 (encoding pro-BMP-2). The ratio of phosphorylated Smad proteins was examined by immunoblotting of whole cell lysates. Data represent the mean with standard error of four independent experiments (top panel), and the HTRA1 proteins were stained with anti-V5 antibody (bottom panel).

FIG. 7

Effects of TGF-β on NOG mRNA Expression in Cultured Skin Fibroblasts.

Cultured skin fibroblasts from healthy Japanese subjects (n=3) were treated with recombinant TGF-β1 at 0.04-5.0 ng/ml for 2 hours. NOG mRNA levels as a fold change of levels in cells without TGF-β1. The bars represent the standard errors.

FIG. 8

Immunohistochemical Analysis in Cerebral Small Arteries.

In panels A, B, and C, small cerebral arteries of autopsied subject II-3, family 5 (homozygous for the A252T mutation) show increased expression of an extra domain-A of fibronectin (panel A) and a versican in intima (panel B) and increased expression of TGF-β1 in media (panel C).

FIG. 9 mRNA Expression of Extra Domain-A of Fibronectin in Cerebral Small Arteries.

In situ hybridization was carried out on the small cerebral arteries of autopsied subject II-1, family 6 (homozygous for the R302X mutation) with the use of antisense (panels A and C) and sense probes (panels B and D) derived from an extra domain-A of fibronectin. Panels E and F, in situ hybridization analysis of extra domain-A of fibronectin antisense probe in the cerebral small arteries of autopsied control subject (40-year-old female with amyotrophic lateral aclerosis).

REFERENCES

1. Chui H C. Subcortical ischemic vascular dementia. Neurol Clin 2007; 25:717-40.
2. Joutel A, Corpechot C, Ducros A, et al. Notch3 mutations in CADASIL, a hereditary adult-onset condition causing stroke and dementia. Nature 1996; 383:707-10.
3. Richards A, van den Maagdenberg A M, Jen J C, et al. C-terminal truncations in human 3'-5' DNA exonuclease TREX1 cause autosomal dominant retinal vasculopathy with cerebral leukodystrophy. Nat Genet 2007; 39:1068-70.
4. Gould D B, Phalan F C, van Mil S E, et al. Role of COL4A1 in small-vessel disease and hemorrhagic stroke. N Engl J Med 2006; 354:1489-96.
5. Revesz T, Ghiso J, Lashley T, et al. Cerebral amyloid angiopathies: a pathologic, biochemical, and genetic view. J Neuropathol Exp Neurol 2003; 62:885-98.
6. Fukutake T, Hirayama K. Familial young-adult-onset arteriosclerotic leukoencephalopathy with alopecia and lumbago without arterial hypertension. Eur Neurol 1995; 35:69-79.
7. Maeda S, Nakayama H, Isaka K, Aihara Y, Nemoto S. Familial unusual encephalopathy of Binswanger's type without hypertension. Folia Psychiatr Neurol Jpn 1976; 30:165-77.
8. Yanagawa S, Ito N, Arima K, Ikeda S. Cerebral autosomal recessive arteriopathy with subcortical infarcts and leukoencephalopathy. Neurology 2002; 58:817-20.
9. Oide T, Nakayama H, Yanagawa S, Ito N, Ikeda S, Arima K. Extensive loss of arterial medial smooth muscle cells and mural extracellular matrix in cerebral autosomal recessive arteriopathy with subcortical infarcts and leukoencephalopathy (CARASIL). Neuropathology 2008; 28:132-42.
10. Okeda R, Murayama S, Sawabe M, Kuroiwa T. Pathology of the cerebral artery in Binswanger's disease in the aged: observation by serial sections and morphometry of the cerebral arteries. Neuropathology 2004; 24:21-9.
11. Tanoi Y, Okeda R, Budka H. Binswanger's encephalopathy: serial sections and morphometry of the cerebral arteries. Acta Neuropathol 2000; 100:347-55.
12. Lathrop G M, Lalouel J M, Julier C, Ott J. Strategies for multilocus linkage analysis in humans. Proc Natl Acad Sci USA 1984; 81:3443-6.
13. Cottingham R W, Jr., Idury R M, Schaffer A A. Faster sequential genetic linkage computations. Am J Hum Genet 1993; 53:252-63.
14. Hu S I, Carozza M, Klein M, Nantermet P, Luk D, Crowl R M. Human HtrA, an evolutionarily conserved serine protease identified as a differentially expressed gene product in osteoarthritic cartilage. J Biol Chem 1998; 273:34406-12.

15. Oka C, Tsujimoto R, Kajikawa M, et al. HtrA1 serine protease inhibits signaling mediated by Tgfβ family proteins. Development 2004; 131:1041-53.
16. Katagiri T, Imada M, Yanai T, Suda T, Takahashi N, Kamijo R. Identification of a BMP-responsive element in Id1, the gene for inhibition of myogenesis. Genes Cells 2002; 7:949-60.
17. Brunner A M, Marquardt H, Malacko A R, Lioubin M N, Purchio A F. Site-directed mutagenesis of cysteine residues in the pro region of the transforming growth factor β 1 precursor. Expression and characterization of mutant proteins. J Biol Chem 1989; 264:13660-4.
18. Hillger F, Herr G, Rudolph R, Schwarz E. Biophysical comparison of BMP-2, ProBMP-2, and the free pro-peptide reveals stabilization of the pro-peptide by the mature growth factor. J Biol Chem 2005; 280:14974-80.
19. De Luca A, De Falco M, Severino A, et al. Distribution of the serine protease HtrA1 in normal human tissues. J Histochem Cytochem 2003; 51:1279-84.
20. Kuzmiak H A, Maquat L E. Applying nonsense-mediated mRNA decay research to the clinic: progress and challenges. Trends Mol Med 2006; 12:306-16.
21. Gazzerro E, Gangji V, Canalis E. Bone morphogenetic proteins induce the expression of noggin, which limits their activity in cultured rat osteoblasts. J Clin Invest 1998; 102:2106-14.
22. Glukhova M A, Frid M G, Shekhonin B Y, et al. Expression of extra domain A fibronectin sequence in vascular smooth muscle cells is phenotype dependent. J Cell Biol 1989; 109:357-66.
23. Leask A, Abraham D J. TGF-β signaling and the fibrotic response. Faseb J 2004; 18:816-27.
24. Schonherr E, Jarvelainen H T, Sandell L J, Wight T N. Effects of platelet-derived growth factor and transforming growth factor-β 1 on the synthesis of a large versican-like chondroitin sulfate proteoglycan by arterial smooth muscle cells. J Biol Chem 1991; 266:17640-7.
25. Grainger D J. Transforming growth factor β and atherosclerosis: so far, so good for the protective cytokine hypothesis. Arterioscler Thromb Vasc Biol 2004; 24:399-404.
26. ten Dijke P, Arthur H M. Extracellular control of TGFβ signalling in vascular development and disease. Nat Rev Mol Cell Biol 2007; 8:857-69.
27. O'Callaghan C J, Williams B. Mechanical strain-induced extracellular matrix production by human vascular smooth muscle cells: role of TGF-β(1). Hypertension 2000; 36:319-24.
28. Liu X, Alexander V, Vijayachandra K, Bhogte E, Diamond I, Glick A. Conditional epidermal expression of TGF Jβ 1 blocks neonatal lethality but causes a reversible hyperplasia and alopecia. Proc Natl Acad Sci USA 2001; 98:9139-44.
29. Botchkarev V A. Bone morphogenetic proteins and their antagonists in skin and hair follicle biology. J Invest Dermatol 2003; 120:36-47.
30. Yoon B S, Lyons K M. Multiple functions of BMPs in chondrogenesis. J Cell Biochem 2004; 93:93-103.
31. Hadfield K D, Rock C F, Inkson C A, et al. HtrA1 inhibits mineral deposition by osteoblasts: requirement for the protease and PDZ domains. J Biol Chem 2008; 283:5928-38.
32. Clausen T, Southan C, Ehrmann M. The HtrA family of proteases: implications for protein composition and cell fate. Mol Cell 2002; 10:443-55.
33. Tsuchiya A, Yano M, Tocharus J, et al. Expression of mouse HtrA1 serine protease in normal bone and cartilage and its upregulation in joint cartilage damaged by experimental arthritis. Bone 2005; 37:323-36.
34. Grau S, Baldi A, Bussani R, et al. Implications of the serine protease HtrA1 in amyloid precursor protein processing. Proc Natl Acad Sci USA 2005; 102:6021-6.
35. Gilicze A, Kohalmi B, Pocza P, et al. HtrA1 is a novel mast cell serine protease of mice and men. Mol Immunol 2007; 44:2961-8.
36. Launay S, Maubert E, Lebeurrier N, et al. HtrA1-dependent proteolysis of TGF-β controls both neuronal maturation and developmental survival. Cell Death Differ 2008; 15:1408-16.
37. Zacchigna L, Vecchione C, Notte A, et al. Emilin1 links TGF-β maturation to blood pressure homeostasis. Cell 2006; 124:929-42.
38. Dewan A, Liu M, Hartman S, et al. HTRA1 promoter polymorphism in wet age-related macular degeneration. Science 2006; 314:989-92.
39. Yang Z, Camp N J, Sun H, et al. A variant of the HTRA1 gene increases susceptibility to age-related macular degeneration. Science 2006; 314:992-3.

INDUSTRIAL APPLICABILITY

The present invention is useful for diagnosing or detecting cerebral autosomal recessive arteriopathy with subcortical infarcts and leukoencephalopathy (CARASIL).

Sequence Free Text

SEQ ID NO:5-20: Synthetic DNA

The invention claimed is:

1. A method of determining the presence of a HTRA1 mutation in a human subject, comprising:
    (a) obtaining a biological sample from a human subject;
    (b) assaying a HTRA1 nucleic acid in the biological sample for a HTRA1 mutation selected from the group consisting of C>T at position 1108 of SEQ ID NO: 1, C>T at position 904 of SEQ ID NO: 1, G>A at position 889 of SEQ ID NO: 1, and G>A at position 754 of SEQ ID NO: 1 by contacting the HTRA1 nucleic acid with a detectably labeled oligonucleotide probe, wherein the detectably labeled oligonucleotide probe comprises a fragment of the complement of SEQ ID NO: 1, wherein the fragment includes an A at position 1108, an A at position 904, a T at position 889, or T at position 754 of SEQ ID NO: 1;
    (c) detecting hybridization of the HTRA1 nucleic acid with the detectably labeled oligonucleotide probe; and
    (d) determining the presence of the HTRA1 mutation comprising a C>T at position 1108 of SEQ ID NO: 1, C>T at position 904 of SEQ ID NO: 1, G>A at position 889 of SEQ ID NO: 1, or G>A at position 754 of SEQ ID NO: 1.

2. The method according to claim 1, wherein the HTRA1 nucleic acid is present in or derived from the biological sample selected from the group consisting of blood, serum, plasma, saliva, cerebral spinal fluid, oral mucosa and nail.

3. The method according to claim 1, wherein the biological sample is blood.

4. The method of claim 1, wherein the mutation is C904T.

* * * * *